United States Patent [19]

Koizumi et al.

[11] Patent Number: 4,740,079
[45] Date of Patent: Apr. 26, 1988

[54] METHOD OF AND APPARATUS FOR DETECTING FOREIGN SUBSTANCES

[75] Inventors: Mitsuyoshi Koizumi; Yoshimasa Ohshima; Minoru Tanaka, all of Yokohama, Japan

[73] Assignee: Hitachi, Ltd., Tokyo, Japan

[21] Appl. No.: 792,320

[22] Filed: Oct. 28, 1985

[30] Foreign Application Priority Data

Oct. 29, 1984 [JP] Japan .................................. 59-225714
Nov. 14, 1984 [JP] Japan .................................. 59-238343

[51] Int. Cl.$^4$ ............................................. G01N 21/01
[52] U.S. Cl. ............................................. 356/237; 250/572; 358/199
[58] Field of Search ............... 356/237, 337, 338, 339, 356/340, 343; 250/563, 572; 358/199, 200

[56] References Cited

U.S. PATENT DOCUMENTS 4,286,293  8/1981  Jablonowski ........................ 358/199
4,441,124  4/1984  Heebner et al. ................. 356/237 X

FOREIGN PATENT DOCUMENTS 0149829  11/1980  Japan .................................. 356/237

Primary Examiner—Eugene R. LaRoche
Assistant Examiner—Robert J. Pascal
Attorney, Agent, or Firm—Antonelli, Terry & Wands

[57] ABSTRACT

The present invention provides a method for detecting foreign substances which detects a foreign substance with a first photoelectric conversion element by emphasizing the foreign substance and detects a background on the object with a second photoelectric conversion element by emphasizing the background and detects a foreign substance detection signal obtained from the first photoelectric conversion element by emphasizing the signal with a detection signal obtained from the second photoelectric conversion element.

9 Claims, 34 Drawing Sheets

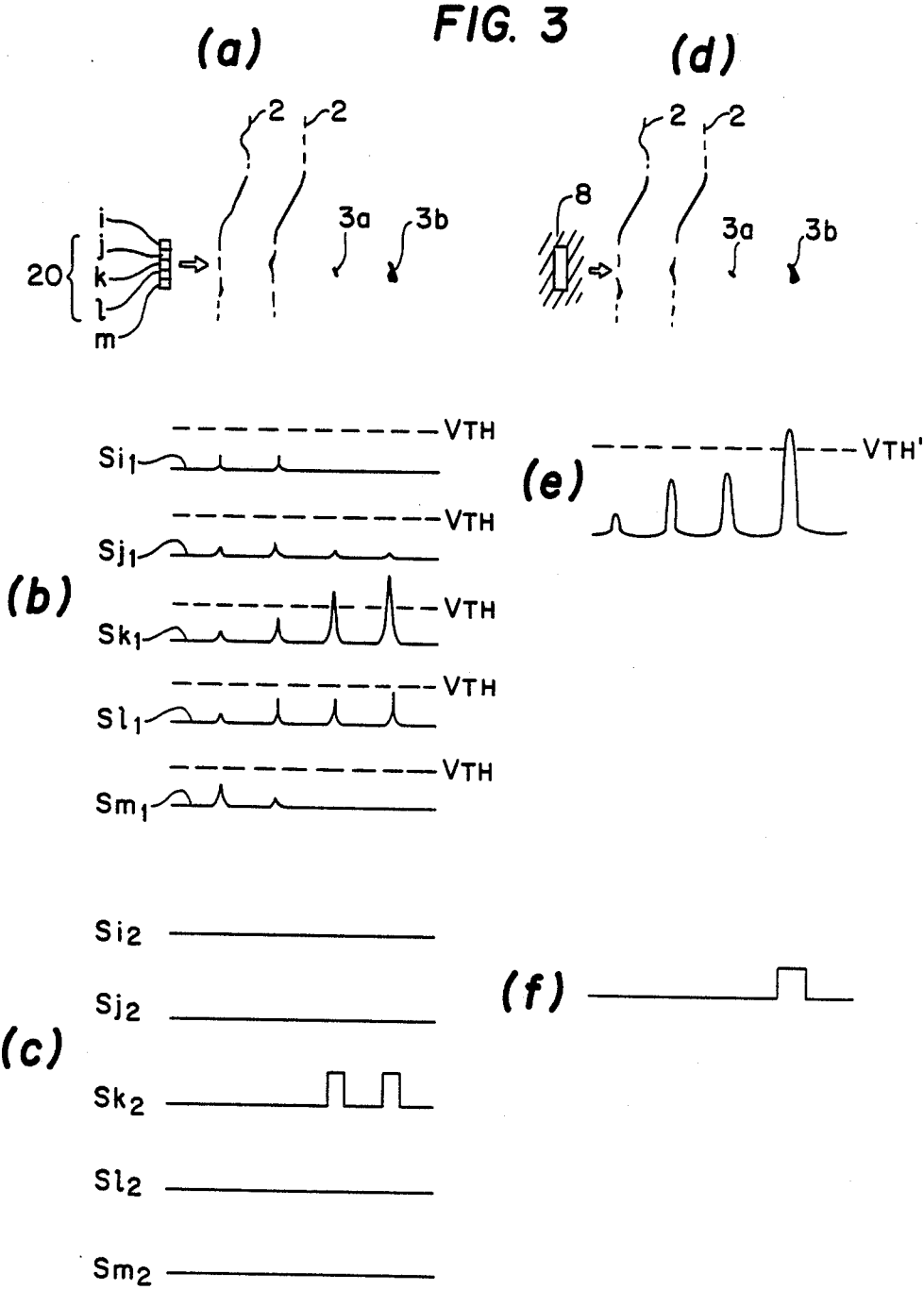

FIG. 6
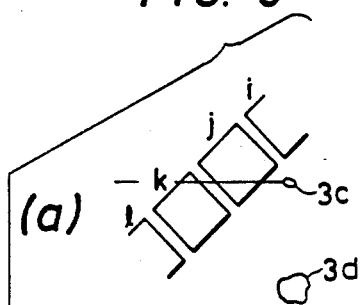
(a)
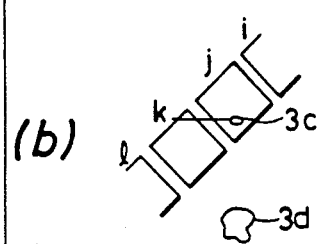
(b)
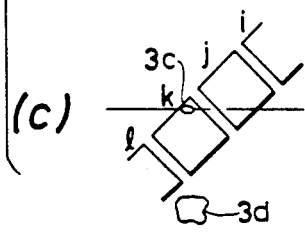
(c)
FIG. 7
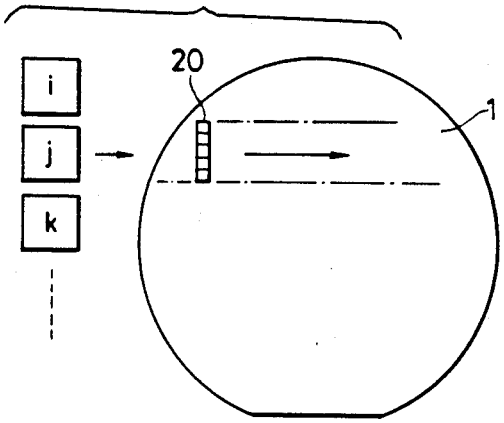
FIG. 8
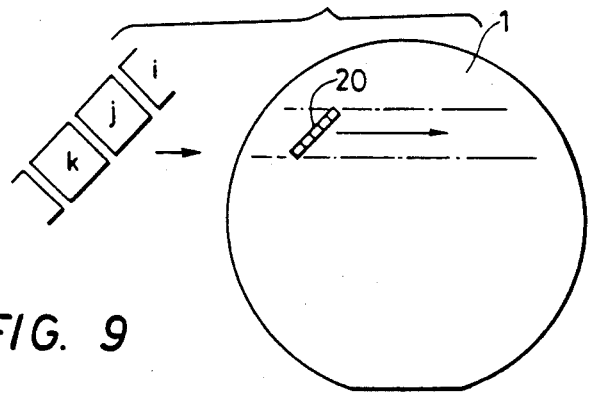
FIG. 9
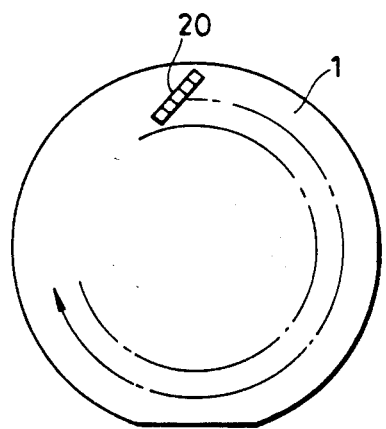

FIG. 18
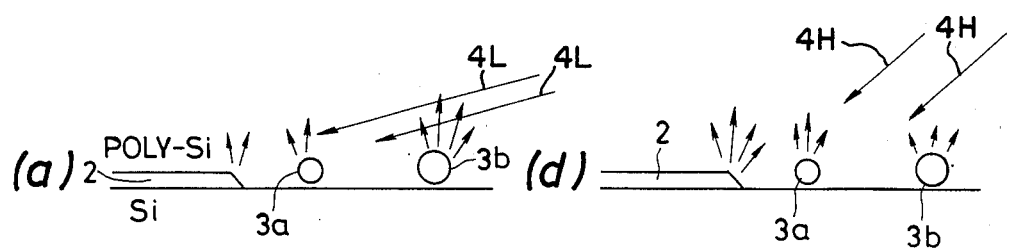
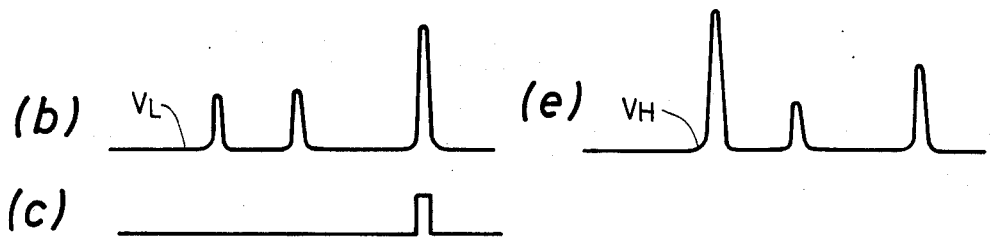
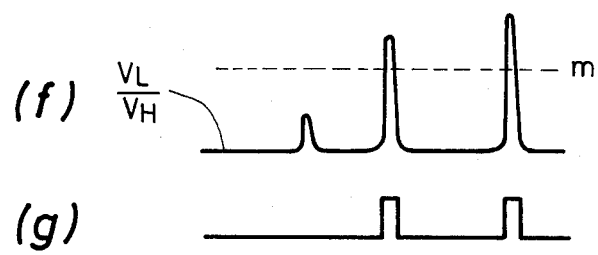

FIG. 32
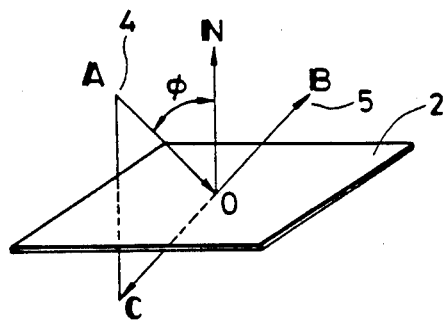
FIG. 33
(a)
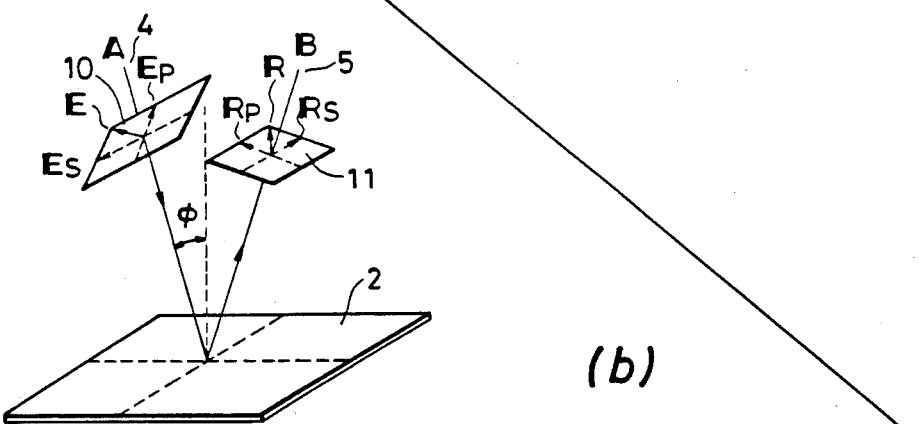
(b)
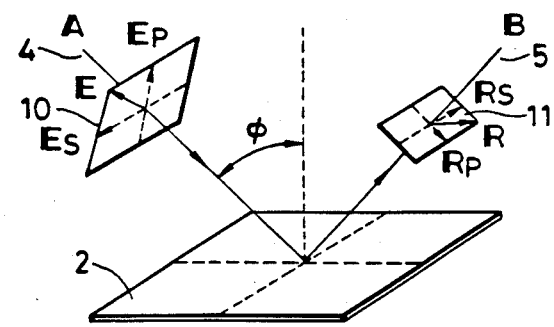

FIG. 34
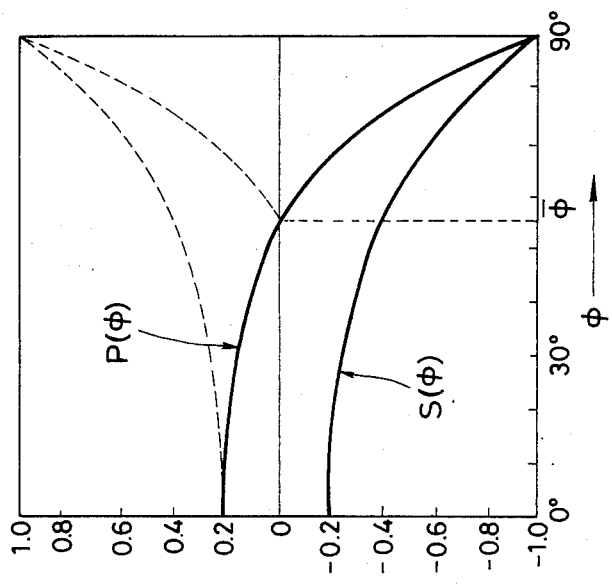
(b)
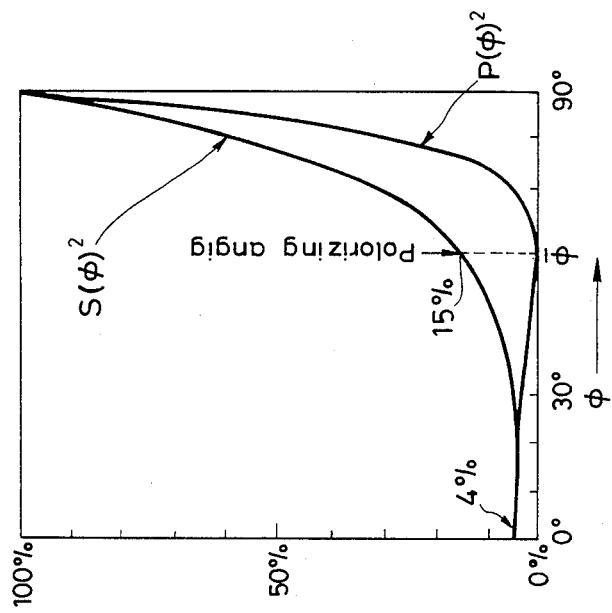
(a)

(a)   (b)

FIG. 37
(a)
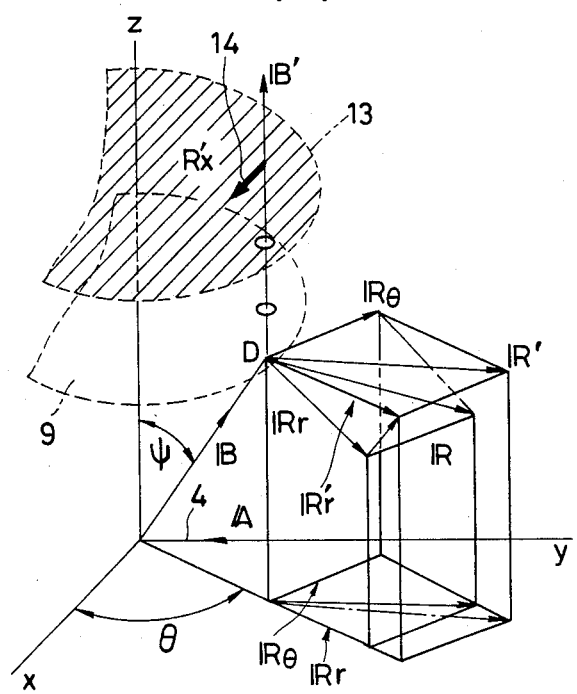
(b)
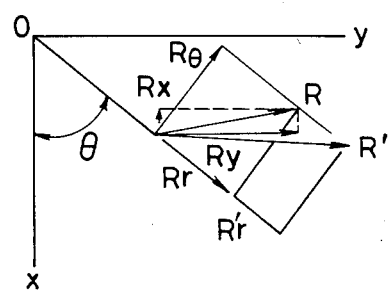

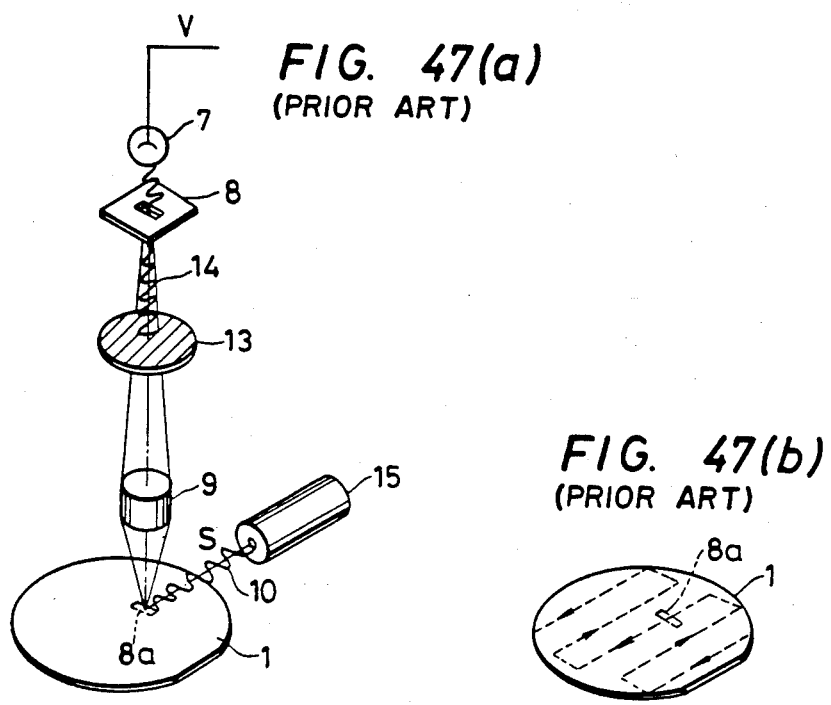
FIG. 47(a) (PRIOR ART)
FIG. 47(b) (PRIOR ART)
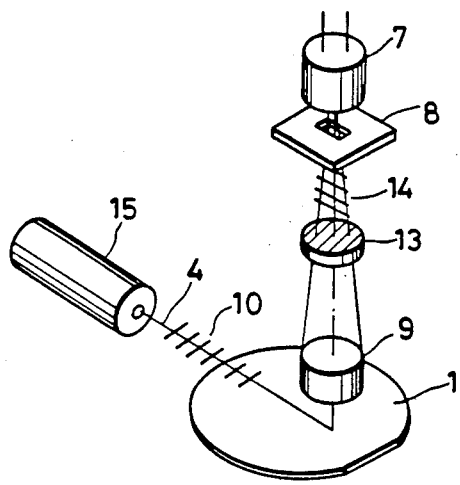
FIG. 50

METHOD OF AND APPARATUS FOR DETECTING FOREIGN SUBSTANCES

BACKGROUND OF THE INVENTION

This invention relates to a method of and apparatus for quickly and sensitively detecting fine foreign substances on a semiconductor LSI wafer or a mask and, more particularly a method and an apparatus for detecting foreign substances on a wafer with a pattern in an intermediate step of an LSI manufacturing process.

With an apparatus for inspecting foreign substances on a wafer of the prior art, the entire surface of the wafer is scanned and inspected by helical scanning performed by:

(I) combination of single dimensional high speed scanning of a laser beam and one dimensional low speed transfer of a specimen; or (II) combination of high speed rotation of a specimen and one dimensional low speed transfer of the specimen.

In Japanese Patent Laid-Open No. 80546/1982 (known precedent 1), the scanning equivalent to above method (I) is realized by combination of electric scanning of a self-scanning type single dimensional photoelectric conversion element array and slow speed transfer of a specimen. Also in the literature by A. D. Gara: Automatic Microcircuit and Wafer Inspection, Electronics Test, vol. 4, No. 5, May 1981, p. 60~p. 70 (known precedent 2), the scanning equivalent to above method (II) is realized by combination of a self-scanning type single dimensional photoelectric conversion element array provided at the position of a wafer radius and the rotating movement of a specimen.

However, because a non-sensitive zone exists adjacent to each picture element of the photoelectric conversion element, with the methods of known precedents 1 and 2, if a foreign substance is scanned by the non-sensitive zone, the substance will certainly be dispensably overlooked. In order to avoid this, it is necessary to provide an overlapped arrangement of a plurality of photoelectric conversion element arrays so as to cover all non-sensitive zones. This arrangement unnecessarily increases the number of signal processing circuits and causes deterioration of reliability. However, if size of a foreign substance to be detected is large enough compared to the width of above non-sensitive zone, or if the summation of the widths of the non-sensitive zones is small enough to be neglected compared to the summation of the widths of the picture elements of the photoelectric conversion element, the failure to detect mentioned above will not be a significant problem and overlapping of the photoelectric conversion element arrays will not be necessary. From such point of view, the failure to detect by the non-sensitive zone is neglected in the methods of known precedents 1 and 2.

(Detection of Foreign Substances on a Wafer with a Pattern)

It is indispensable for improvement of yield and reliability to inspect foreign substances on a wafer with a pattern in an intermediate step of an LSI manufacturing process. The automation of such inspection is realized by inspection methods employing polarized light as described in a series of Japanese Patents; Laid-Open No. 30630/1981, Laid-Open No. 149829/1980, Laid-Open No. 101390/1979, Laid-Open No. 94145/1980 and so on. The principles of the inspection methods are hereinunder described with reference to FIG. 43 through FIG. 50.

As shown in FIG. 43, if illuminating light 4 is simply applied to a surface of a wafer 1 with an inclination angle of $\phi$, reflected light 5 from a pattern 2 and scattered light 6 from a foreign substance 3 are produced simultaneously so that it is impossible to detect the foreign substance 3 discriminating from the pattern 2. Then a device wherein a polarized laser beam is employed as the illuminating light to detect the foreign substance 3 is proposed.

As shown in FIG. 44(a), an S polarized laser beam 4 is applied to the pattern 2 on the wafer 1 (wherein the laser beam 4 whose electrical vector 10 is parallel to the wafer surface is called an S polarized laser beam). Generally speaking, surface roughness of the pattern 2 is microscopically small enough compared to the wavelength of the illuminating light and the surface can be considered to be optically smooth so that the reflected light 5 holds also an S polarized light component 11. Therefore, if an analyzer 13 which shuts S polarized light off is provided in a light passage of the reflected light 5, the reflected light 5 is shut off and can not reach a photoelectric conversion element 7. As shown in FIG. 44(b), the scattered light 6 from the foreign substance 3 includes not only the S polarized light component 11 but also a P polarized light component 12 because the surface of the foreign substance 3 is rough and the P polarized light component 12 is produced as a result of dissolution of the polarization. Therefore, if the P polarized light component 14 which transmits through the analyzer 13 is detected by the photoelectric conversion element 7, the foreign substance 3 can be detected.

As shown in FIG. 43, if an angle between the direction of the reflected light 5 from the pattern 2 is a right angle, the reflected light 5 is completely shut off by the photodetection element, but if the angle is not a right angle, the reflected light 5 is not completely shut off. This investigation is described in Transactions of Institute of Measurement and Automatic Control, Vol. 17, No. 2, 1981, p. 232~p. 242. According to this literature, the reflected light with an angle within ±30° deviation from a right angle only enters an object lens provided above the wafer. Therefore, although the reflected light 5 from the pattern within such range of the angle is not completely shut off by the analyzer, the intensity is small enough to be discriminated from the scattered light from the foreign substance of $\phi$ 2~3 $\mu$m so that there is no problem in practice.

In this case, the inclination angle of the polarized laser beam 4 is predetermined to be about 1°~3°. The reason for this selection is hereinunder described.

In an experiment shown in FIG. 45, an intensity $V_s$ of a component 14 of scattered light from a foreign substance of $\phi$ 2 $\mu$m which transmitted through the analyzer 13 was measured by an object lens 9 (magnification 40X, N. A.=0.55). The result of the experiment is shown in FIG. 46. The curve of FIG. 46 was obtained by taking the inclination angle of the laser beam $\phi$ as an abscissa and plotting discrimination ratio $V_s/V_p$ of the foreign substance/the pattern. From this diagram, when the inclination angle $\phi$ is less than 5°, $V_s$ can easily be discriminated from $V_p$ so that stable foreign substance detection is realized. Moreover, taking matters related to design into account, $\phi = 1°~3°$ is the most suitable (reference to Japanese Patent Laid-Open No. 30630/1981).

The purpose of employing two laser sources 15 on the left and right sides is to facilitate stable detection of a foreign substance which produces scattered light with unisotropy.

Then a method for detecting foreign substances employing the detection principle mentioned above is hereinunder described with reference to FIG. 47 through FIG. 50.

In order to limit the domain arm to be detected, a slit 8 is provided in a focus plane for a specimen as shown in FIG. 47. As the scattered light within an area 8a which is the projection of the aperture of the slit 8 on the specimen is detected at a time, if a P component 14d of the scattered light from the foreign substance is large enough compared to the integrated intensity of a P component 14p of the reflected light from the pattern, the foreign substance 3 can be stably detected. Therefore, if the area 8a is about the same size ($2 \sim 3$ $\mu$m) as the foreign substance to be detected, the detection sensitivity will be optimum but the frequency of scanning as shown in FIG. 47 (b) will become large and long inspection time will be required. Conversely, if the area 8a is large, the inspection time will be short but detection sensitivity will be adversely affected. Taking such phenomena into account, foreign substances of $\phi$ $2 \sim 3$ $\mu$m are detected in about 2 minutes (for a wafer of $\phi$ 150 cm) with the area 8a of $100 \times 200$ $\mu$m$^2$ corresponding to the specimen surface at present. The aspect of this inspection is hereinunder described with reference to FIG. 48 and FIG. 49.

FIG. 48 shows a plan view (a) and a sectional view (b) of a wafer surface. There are (I) slightly recessed parts and (II) parts which are not perpendicular to the incident direction of the laser beam 4 and a slight P component 14p of the scattered light is produced by each of such parts. P components 14d which have higher intensity than P components 14p from the parts (I) and (II) mentioned above are produced by small foreign substances 3a of about $\phi$ $0.5 \sim 2$ $\mu$m and large foreign substances of larger than $\phi$ 2 $\mu$m.

FIG. 49 shows an output signal of the photoelectric conversion element 7 when the surface of the sample is scanned by the aperture 8a. In FIG. 49(a), distributions of the P component 14p (circuit pattern) and the P component 14d (foreign substance) on the specimen are shown. If the aperture 8a scans on these distributions, an image signal output V as shown in FIG. 49(b) is obtained and by binarizing the signal output V, the defect signal as shown in FIG. 49(c) is obtained. In this example, the output from the small foreign substance 3a and the output from the edge of the pattern 2 are in the same level and the threshold shown by a broken line must be predetermined at a higher level than those output levels so that the detection is limited only for the large foreign particles.

However, in manufacture of LSIs with high integrity represented by 256 Kbit memory LSI, existence of foreign substances of $\phi$ 1 $\mu$m size have significant influence on production yield. Therefore, detection sensitivity for foreign substances of $\phi$ 1 $\mu$m is required. If the aperture 8a in the apparatus shown in FIG. 47 is limited to be smaller than $5 \times 5$ $\mu$m$^2$, the integral effect of the P components of the scattered light from (I) and (II) mentioned above is reduced compared to the integral effect when the aperture 8a is $10 \times 200$ $\mu$m$^2$. As a result the detection of the foreign substances of $\phi$ 1 $\mu$m is facilitated but the time for inspection is increased by about 40 times and synchronization with production throughput is impossible so that it is difficult to put this method into practical use.

SUMMARY OF THE INVENTION

It is an object of the present invention to provide a method of and an apparatus for inspecting fine foreign substances with high speed discriminating from a circuit pattern.

It is also an object of the present invention to provide a highly reliable and sensitive method for detecting fine foreign substances, wherein illumination which is only slightly scattered by the foreign substance is employed as well as illumination which is thoroughly scattered and, taking into consideration the fact that the latter illumination tends to produce scattered light on the foreign substance and the former illumination tends to produce scattered light on the pattern, the ratio of scattered light signals of two forms of illumination is detected.

It is also an object of the present invention to provide a highly sensitive method for detecting foreign substances without adversely affecting high speed detection by employing a plurality of photoelectric conversion solid pickup elements whose picture elements have photodetecting parts with dimensions of $5 \times 5$ $\mu$m corresponding to the specimen surface, and by comparing and processing output signals from respective elements at the same time in parallel.

It is also an object of the present invention to provide a method and an apparatus for detecting foreign substances wherein a linear polarized laser beam is inclined but almost parallel to a surface of a specimen and the linear polarized laser beam is applied onto the surface of the specimen with its electrical vector being parallel or perpendicular to the surface of the specimen and scattered light from the specimen surface are optically converged and the light which passes an analyzer which is provided in a converged light passage with its transmission axis parallel to the direction of the laser illumination mentioned above is detected by a photoelectric conversion element. In above description, the term "transmission axis" means an axis whose direction is the direction of the oscillation of the electrical vector which transmits 100% through the analyzer.

BRIEF DESCRIPTION OF THE DRAWINGS

FIGS. 3(a–f) describe the comparison between the present invention and an example of the prior art;

FIGS. 6(a–c) show relation of the position between foreign substances and non-sensitive zones in the present invention;

FIG. 7 shows a relative scanning direction between a wafer and the solid pickup element shown in FIG. 5;

FIG. 8 shows a relative scanning direction between a wafer and the solid pickup element shown in FIG. 6;

FIG. 9 shows a relative spiral scanning between a wafer and a solid pickup element;

FIGS. 18(a–g) show output signals or the like obtained by an apparatus shown in FIG. 17;

FIG. 32 is a perspective view showing incident light A and reflected light B of the pattern;

FIGS. 33(a–b) are a perspective view of polarized light of the incident light and the reflected light;

FIGS. 34(a–b) are a set of graphs showing calculated examples of coefficients $s(\phi)$ and $p(\phi)$;

FIGS. 37(a–b) are a perspective view showing a relation between the reflected light B and an object lens;

FIGS. 47(a–b) are a perspective view showing briefly a second example of a method for detecting foreign substances of the prior art;

FIG. 50 is a perspective view showing briefly a method for detecting foreign substances like the second example shown in FIG. 47.

DESCRIPTION OF THE PREFERRED EMBODIMENT

An embodiment of the present invention will be hereinafter described with reference to FIG. 1 through FIG. 13.

Figure 1:
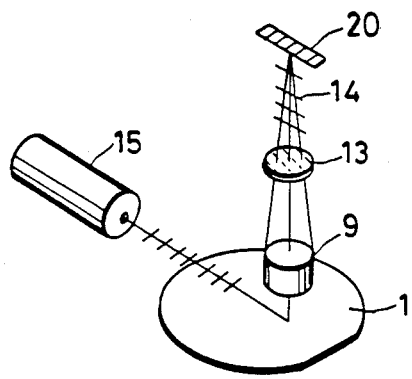
FIG. 1 shows a constitution of one embodiment of an apparatus for inspecting foreign substances of the present invention.

FIG. 1 shows a constitution in which a slit 8 is substituted by a solid pickup element array 20.

Figure 2A:
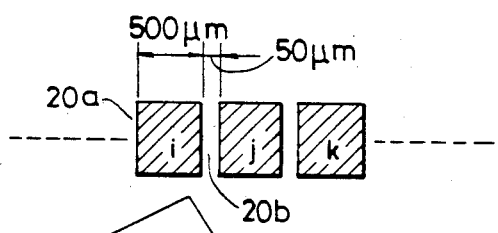
FIGS. 2a and 2b are perspective views showing details of a solid pickup element given in FIG. 1.
Figure 2B:
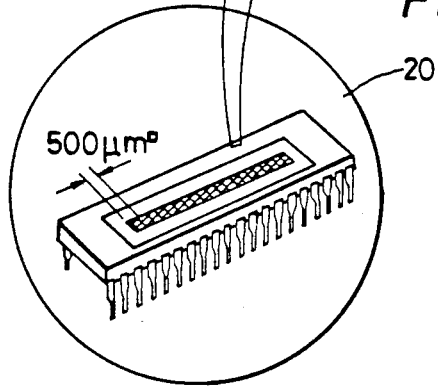

FIG. 2 describes an example of the solid pickup element array 20. Photodetecting parts 20a are silicon photodiodes or GaAsP photodiodes and especially those diodes of the P-I-N junction type are most suitable for the application of the present invention with their high speed responsiveness and high sensitivity characteristics. The width of each photodetecting part 20a (picture element) is 500 μm and there is a non-sensitive zone of the width of 50 μm between adjacent picture elements. When the array has 40 picture elements, if, for instance, an integral magnification of a detection system is 100×, wherein a magnification of an object lens is 40× and that of a relay lens (not shown) is 2.5×, the size of one picture element is 5×5 μm² on a specimen surface. Ultimately a range of 5×220 μm² is scanned while being inspected and the speed of inspection is about the same as that of the prior art.

The effect of the solid pickup element array 20 is described in FIG. 3. For comparison, the effect of the example of the prior art shown in FIG. 50 is shown in FIG. 3(d), FIG. 3(e) and FIG. 3(f) on the right side. In FIG. 3(a), FIG. 3(b) and FIG. 3(c) on the left side, effect of the solid pickup element array is shown but, for simplicity, the number of picture elements in this example is 5 (i, j, k, l, m). FIG. 3(a) shows scanning by the solid pickup element array 20 and FIG. 3(b) shows image signals ($S_{i1}$, $S_{j1}$, $S_{k1}$, $S_{l1}$, $S_{m1}$) and FIG. 3(c) shows signals ($S_{i2}$, $S_{j2}$, $S_{k2}$, $S_{l2}$, $S_{m2}$) binarized with a threshold $V_{TH}$. If an output signal $S_{k1}$ is binarized with the threshold $V_{TH}$, the binarized signal $S_{k2}$ becomes "1" even if a foreign substance 3a is small so that improved sensitivity compared to the prior art is obtained.

Figure 4:
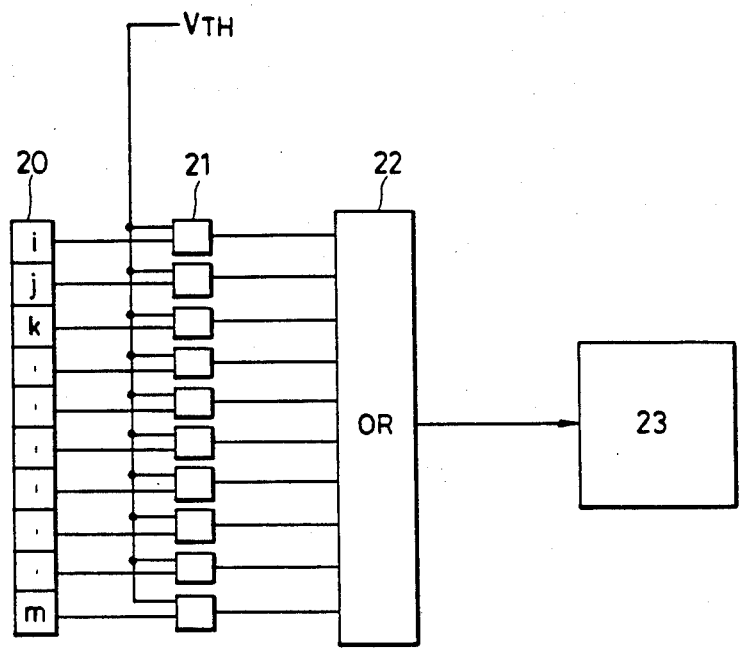
FIG. 4 shows a signal processing circuit of the solid pickup element given in FIG. 1.

FIG. 4 shows a method for processing the signal from each picture element of the solid pickup element array 20. Respective outputs from the picture elements (i)~(m) are binarized by a binarizing circuit 21 in parallel at the same time and a binarized signal ("1") is introduced into an OR circuit 22 and, when a foreign substance is detected by at least one picture element, an output of the OR circuit becomes "1" and is put into a foreign substance memory 23. With this method, outputs of 40 picture elements are processed at the same time in parallel. Therefore, significant improvement of inspection speed and detection sensitivity compared to the method employing a self-scanning pickup element is obtained.

However, the non-sensitive zone 20b of the solid pickup element array 20 has a disadvantage which will be described shortly. Countermeasures for this disadvantage are shown in FIG. 6.

Figure 5:
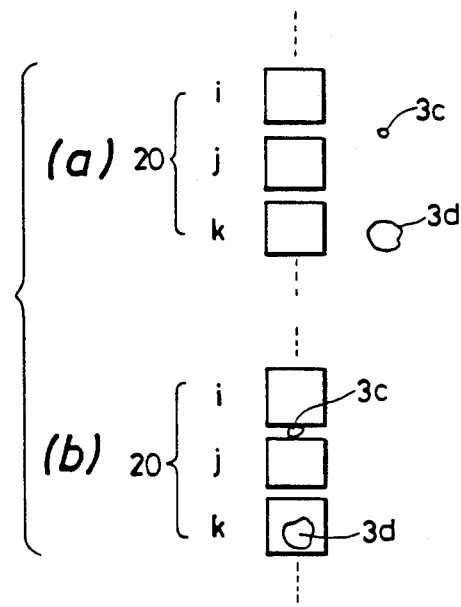
FIGS. 5(a–b) show relation of the position between foreign substances and non-sensitive zones.

If the direction of the arrangement of the solid pickup element array 20 and the direction of scanning make a right angle between them as shown in FIG. 5 and FIG. 7 and if the relation between a non-sensitive zone 20b between picture elements (i) and (j) and a small foreign substance 3c is as shown in FIG. 5, the small foreign substance 3c is overlooked. In FIG. 5, scanning is made from (a) to (b). Then, if an adequate angle, for instance 45°, is provided between the direction of the arrangement of the solid pickup element array and the direction of scanning, such overlooking is avoided. In the case of FIG. 6, scanning is made from (a) to (b) and (b) to (c). If the form of a picture 20 is rectangular, this angle need not be 45°.

In FIG. 8, the small foreign substance 3c is detected twice by picture elements (j) and (k). But this double counting can be avoided by the methods described in Japanese Patents Laid-Open No. 132549/1981, Laid-Open No. 118187/1981, Laid-Open No. 66345/1982, Laid-Open No. 126747/1981 and Laid-Open No. 118647/1981.

FIG. 9 shows an example of the application of the present invention when spiral scanning is employed.

Figures 10, 11:
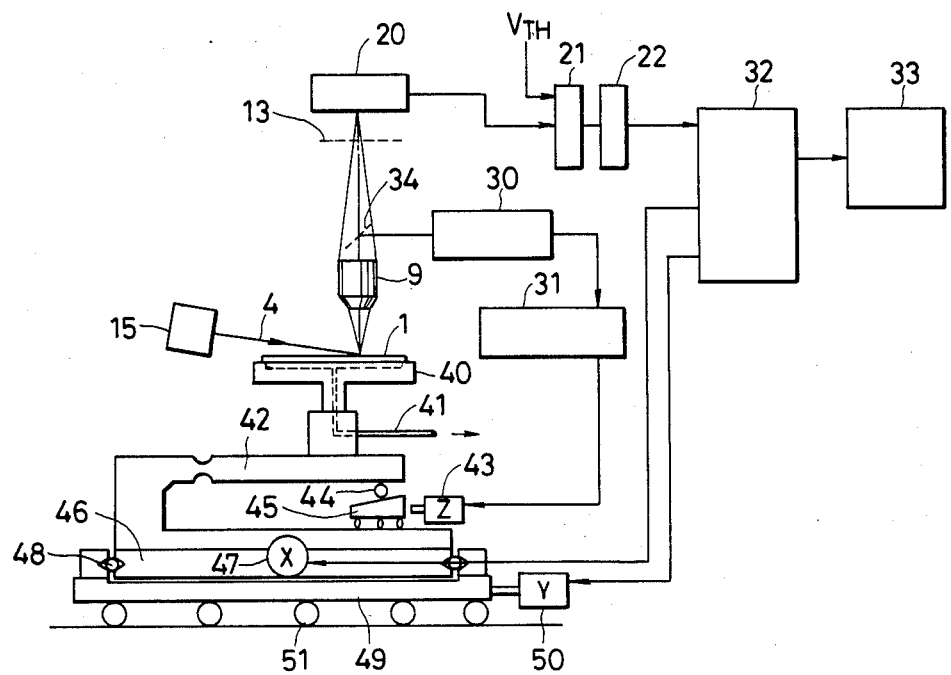
FIG. 10 shows a more definite constitution of the embodiment shown in FIG. 1.
FIG. 11 is a perspective view showing an automatic focus detecting part given in FIG. 10.
Figure 12:
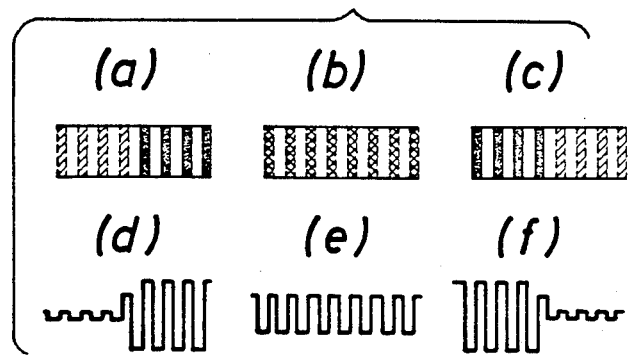
FIGS. 12(a–f) describe the automatic focus detection.

FIG. 10 shows a whole constitution of an embodiment of the present invention. A wafer 1 is transferred to XY directions by an X stage 46 and a Y stage 49 while being attracted to a wafer chuck 40 by a vacuum tube 41. Foreign substance information detected by a solid pickup element array 20 is transferred to a control circuit 32 including a foreign substance memory 23 through a binarizing circuit 21 and an OR circuit 22 and displayed by a display apparatus 33.

Since a picture element is about $5 \times 5$ $\mu m^2$ or smaller in the present invention, if the device is even slightly out of focus due to an irregular wafer surface, the sensitivity of the foreign substance detection is adversely affected. Therefore, this problem with focus must be detected by an automatic focus detecting part 30 during the inspection and fed-back to a driver 31 of a focusing mechanism motor 43. The principle of this automatic focusing mechanism is presented on p. 223~p.224 of the 22nd SICE Scientific Lecture Meeting Text and described in Japanese Patent Laid-Open No. 70540/1983. This principle is hereinunder described with reference to FIG. 11 through FIG. 13. This method is most suitable for the present invention because it facilitates stable automatic focusing without being influenced by a pattern on a specimen.

FIG. 11 shows a main part of the automatic focus detecting part 30. Stripe patterns 60a and 60b on stripe pattern glass plates are projected on a specimen by an object lens 9. Focus positions of the stripe patterns 60a and 60b are predetermined to be a little higher or a little lower than a focus position of the pickup element array 20. The images of the respective stripe patterns 60a and 60b on the specimen are enlarged by the object lens 9 and reflected by half mirrors 34 and 62 and their images are focused on a pickup element 61.

FIG. 12(a) shows images of projected stripe patterns focused on the pickup element 61 when the wafer is too low (Z<0) and FIG. 12(d) shows waveforms of image signals detected by the pickup element 61 in the case of FIG. 12(a). FIG. 12(b) shows images of projected stripe patterns focused on the pickup element 61 when the wafer is at the focus position (Z=0) and FIG. 12(e) shows waveforms of image signals detected by the pickup element 61 in the case of FIG. 12(b). FIG. 12(c) shows images of projected stripe patterns focused on the pickup element 61 when the wafer is too high (Z>0) and FIG. 12(f) shows waveforms of image signals detected by the pickup element 61 in the case of FIG. 12(c).

Therefore, when the pickup element array 20 is at the focus position, signals detected by the pickup element 61 corresponding to the stripe patterns 60a and 60b are identical so that the differential signal of the two signals becomes zero.

Figure 13:
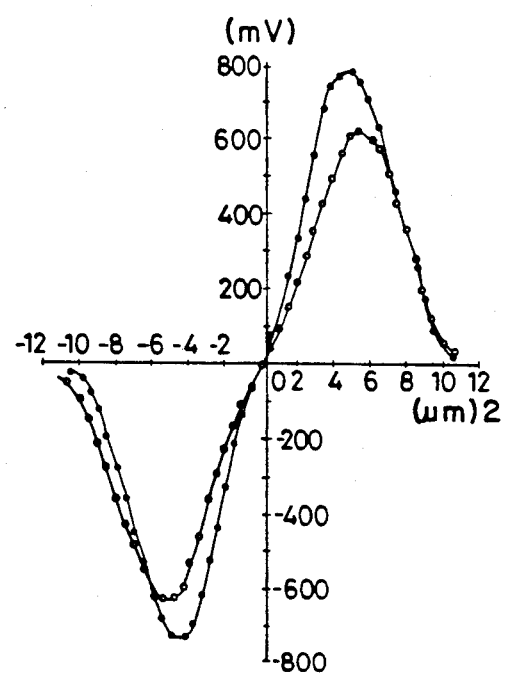
FIG. 13 shows a relation between a differential output and a discrepancy of a focus obtained from the automatic focus detecting part shown in FIG. 11.

If the wafer is too high (or too low), the discrepancy of the pickup element 61 from the focus position corresponds to an output of the differential signal so that a servo signal shown in FIG. 13 is obtained. In FIG. 13, measured examples of the differential signals when the specimen surface is a patterned surface (memory cell surface). With this constitution, focusing within $\pm 0.5$ $\mu m$ is possible and, when the magnification of the object lens is $40 \times$, stable foreign substance detection is facilitated. As the automatic focusing mechanism, for instance, a simple constitution comprising a motor 33, a slope 45, a ball 44 and a spring board 42 may be employed.

Then descriptions corresponding to claims of the present invention are hereinunder described with reference to FIG. 14 through 29.

Figure 14:
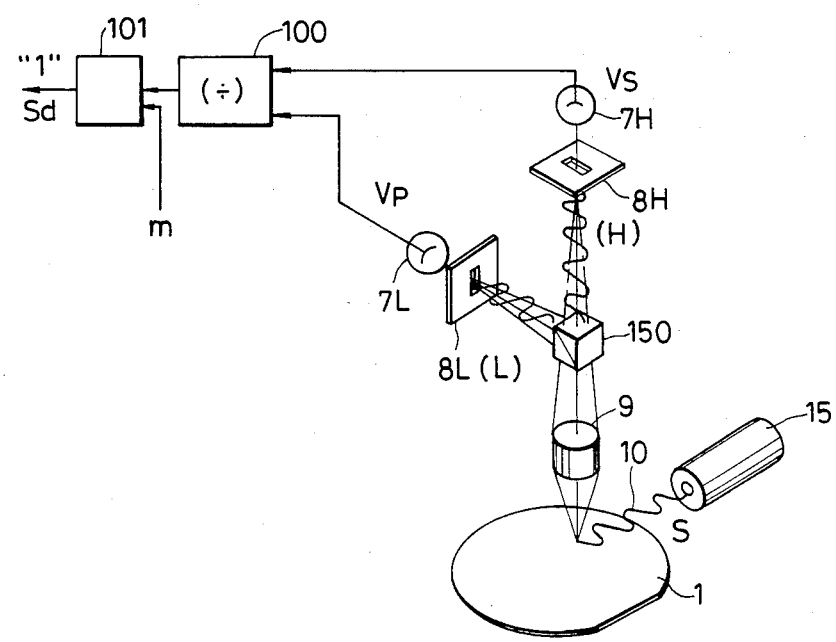
FIG. 14 is a perspective view describing a principle of the present invention.
Figure 15:
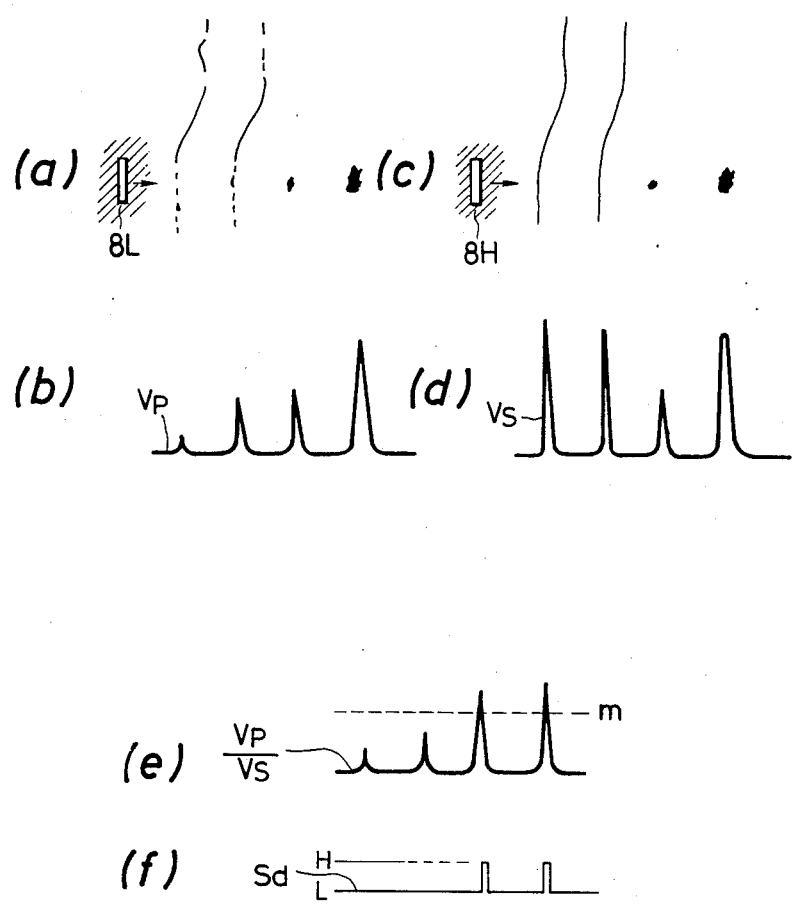
FIGS. 15(a–f) show scanning on a wafer and output signals obtained by an apparatus shown in FIG. 14.
Figure 49:
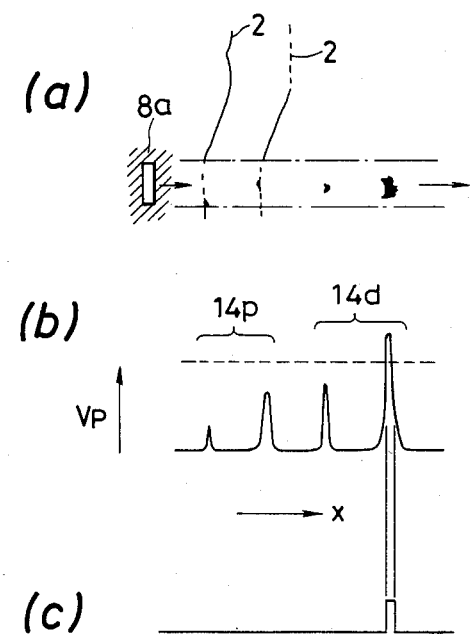
FIGS. 49(a–c) show relations of image signals obtained by scanning a wafer with a slit.

A basic principle is hereinunder described with reference to FIG. 14 and FIG. 15. If a photodetecting element 13 is removed and a polarized beam splitter 150 is provided in the constitution shown in FIG. 47, the constitution shown in FIG. 14 is obtained. Slits 8H and 8L detect an identical point on the specimen. As the polarized beam splitter 150 has a characteristic with which polarized light component P is reflected and polarized light component S is transmitted, an output $V_p$ of a photoelectric conversion element 7L is identical to the output (FIG. 49) in the case of FIG. 47. The output shown in FIG. 49 is transferred into FIG. 15(a) and (b). On the other hand, an output $V_s$ of a photoelectric conversion element 7H in the case of scanning shown in FIG. 15(c) is as shown in FIG. 15(d). Comparing FIG. 15(a) and (b) and FIG. 15(c) and (d), it is understood that in the case of FIG. 15(a) and (b) the output from the foreign substance is higher than that from the pattern and in the case of FIG. 15(c) and (d) the output from the pattern is higher. Therefore, it is understood that the small foreign substance 3a (which can not be detected by the binarization in the case of FIG. 49) can be detected if the ratio of two output values $V_p/V_s$ is processed (shown in FIG. 15(e)) by an analog comparing circuit 100 and binarized by a binarizing circuit 101 with a threshold (m) (shown in FIG. 15(f)). Moreover, if the solid pickup element arrays 20H and 20L are employed in place of the photoelectric conversion elements 7H and 7L, the detection sensitivity can be improved. In this case, a plurality of the analog comparing circuits 100 and the binarizing circuits 101 must be employed to perform simultaneous, parallel analog comparison (reference to FIG. 16).

The illuminating and detecting method mentioned above is called type (II) illumination.

Figure 17:
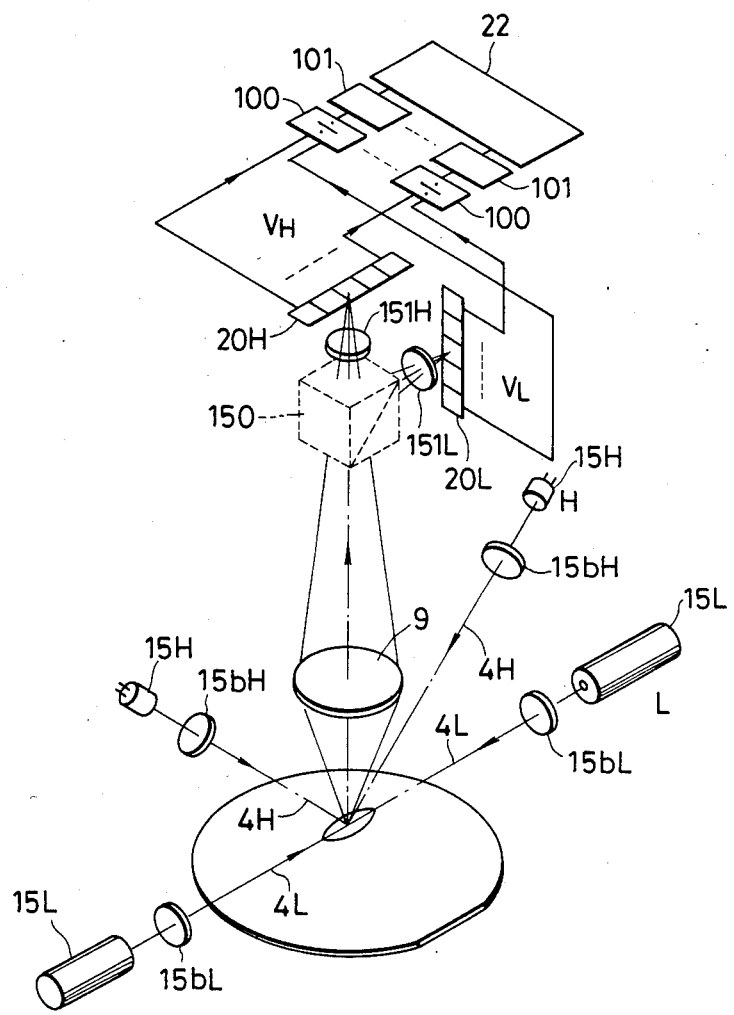
FIG. 17 is a perspective view showing an embodiment of the apparatus shown in FIG. 14 with a solid pickup element array as a photoelectric conversion element and with an illumination of type (I)
Figure 46:
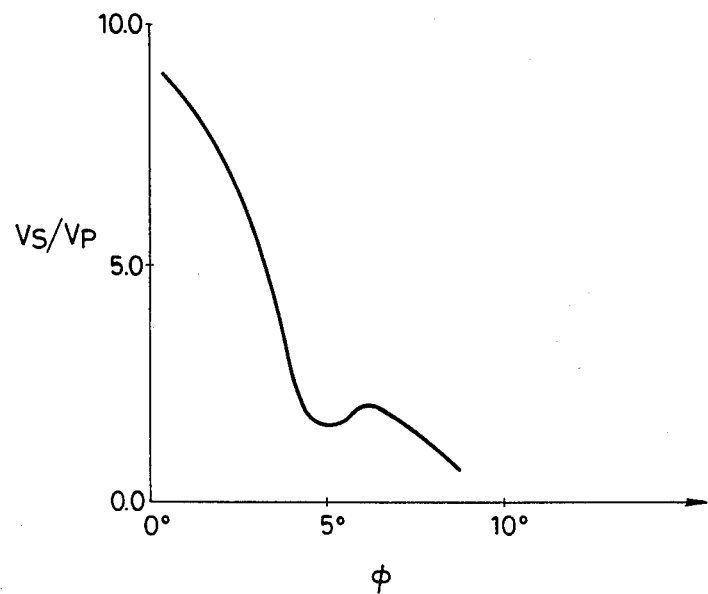
FIG. 46 is a graph showing data of output ratio $V_s/V_p$ when an illumination angle $\phi$ is changed.
Figure 48:
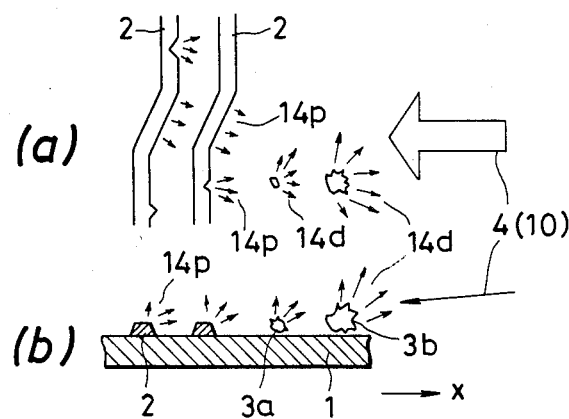
FIGS. 48(a–b) show situations of reflection from a circuit pattern and foreign substances on the wafer.

Then type (I) illumination is hereinunder described with reference to FIG. 17 and FIG. 18. This means the method wherein only P components are detected and compared by utilizing output characteristics of the foreign substance and the pattern in accordance with an inclination angle $\phi$ shown in FIG. 46. For instance, as shown in FIG. 17, low angle S polarized illuminating light 15L (wavelength $\lambda_1$) and high angle S polarized illuminating light 15H (wavelength $\lambda_2$) are applied to the same point on the specimen and only P components are detected and compared by arrays 20H and 20L with a spectrum diverging prism 150 and analyzer 151H and 151L. The outputs and the binarizing method of the arrays 20H and 20L are shown in FIG. 18.

FIG. 18(a) describes the case when laser beams are applied onto, for instance, a silicon wafer on which foreign substances 3a and 3b exist with low inclination angle.

FIG. 18(b) shows an output signal $V_L$ in such case and FIG. 18(c) shows a binarized signal of the signal. FIG. 18(d) describes the case when laser beams are applied onto, for instance, a silicon wafer with high inclination angle. FIG. 18(e) shows the output signal $V_H$ in such case. FIG. 18(f) shows signal wave of $V_L/V_H$ and FIG. 18(g) shows binarized signal in such case.

Figure 30:
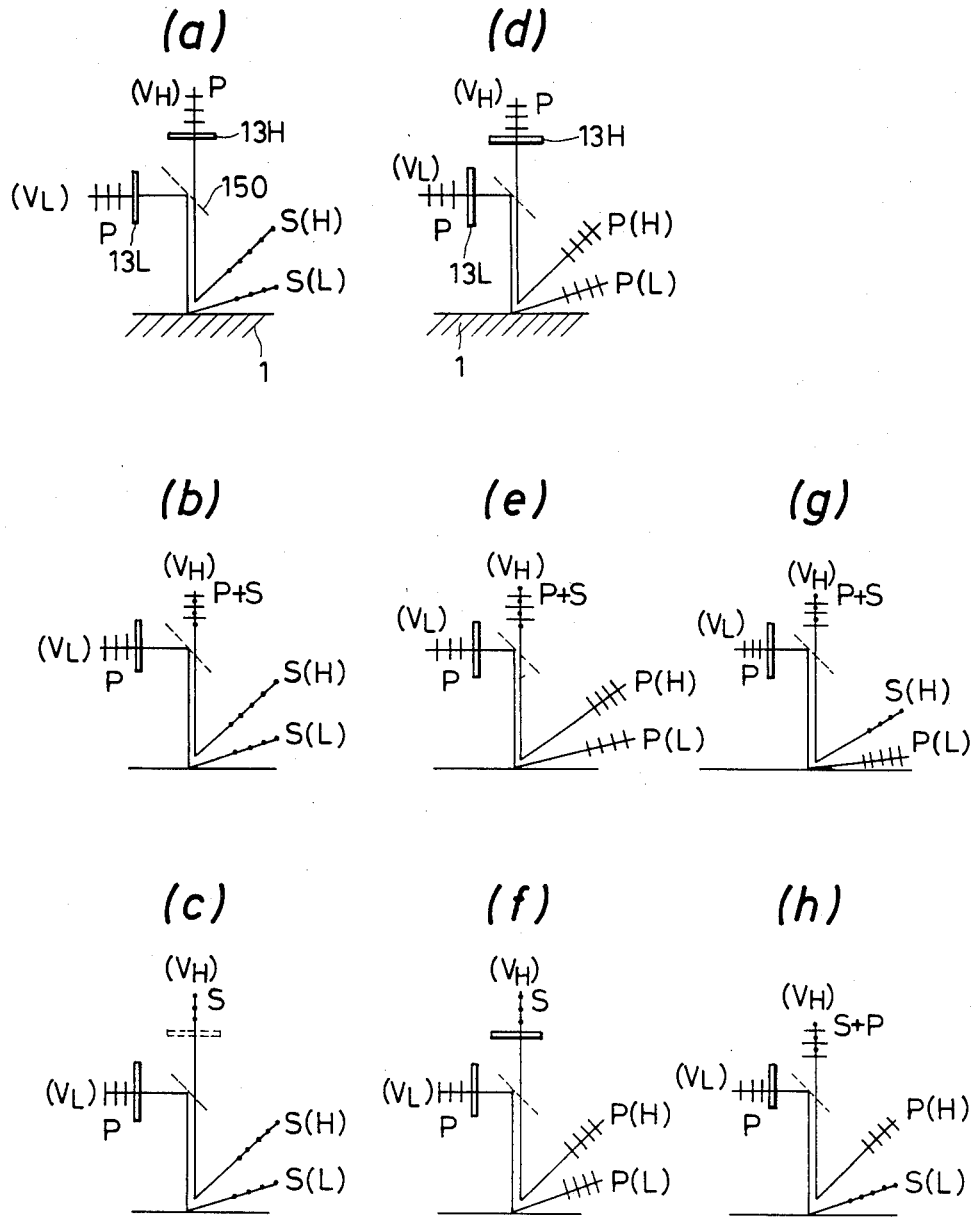
FIGS. 30(a–h) and FIGS. 31(a–d) show various conbinations of illumination and photodetection.

FIG. 30 shows models of illumination and analyzed detection conditions mentioned above. In the case of type (I) illumination, not only the S polarized illuminating lights 15L and 15H mentioned above but also various conditions of illuminating lights and detecting lights shown by FIG. 30(b)~(h) and FIG. 31(a)~(d) can be employed. In these models, (A) S polarized light illumination and P polarized light component detection or (B) P polarized light illumination and P polarized light component detection is employed as the illumination and analyzed detection condition (L) which emphasizes the foreign substances. The reason for this employment will be described in detail later.

Any conditions other than (A) and (B) mentioned above can be employed as illumination and analyzed detection (H) which emphasizes the pattern and employment of polarized light is not necessary. In other words, incoherent light such as light from a typical halogen lamp may be employed and such light is denoted by the symbol S+P in FIG. 31(a)~(d).).

As the spectrum diverging prism 150 mentioned above, a dichroic prism or mirror described in Japanese Patents Laid-Open No. 149829/1980 and Laid-Open No. 43539/1981 may be provided or a combination of a light diverging prism, a half mirror, and a color filter or an interference filter may be employed.

If any two laser sources among a He-Ne laser ($\lambda = 6,320$ Å), a GaAlAs laser diode ($\lambda = 7,800$ Å~8,300 Å), an InGaAsP laser diode ($\lambda = 13,000$ Å) and an Ar laser (for instance $\lambda = 4,580$ Å) are selected for the illuminating lights 15H and 15L, the light is converged on the specimen surface by a lens system 15bL so that high illuminance can be obtained and the detection becomes more stable.

As described above, it is absolutely necessary for type (I) illumination that conditions (A) or (B) must be filled for the foreign substances emphasizing illumination (L) and that different wavelengths ($\lambda_1$ and $\lambda_2$) must be employed for the pattern emphasizing illumination (H) and the foreign substance emphasizing illumination (L).

If a method, wherein time sharing detection is applied and detected outputs of (L) and (H) are compared to each other, is employed as described in Japanese Patent Laid-Open No. 66345/1982 instead of spectrum diverging, illumination and detection can be achieved with simple parts for constitution. In this case, only one type of illumination is employed and only one array 20 is enough, but an optical element which has a function of high speed photodetection characteristics switching such as a Pockel cell is indispensable.

Then an embodiment of the present invention is hereinunder described with reference to FIG. 19 through FIG. 28.

Figure 16:
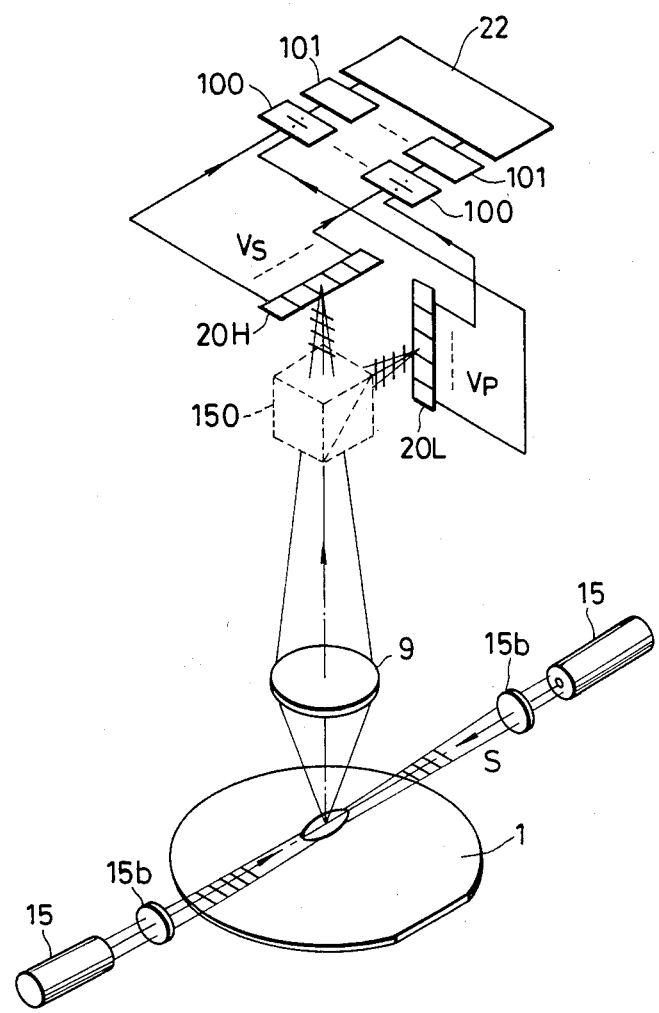
FIG. 16 is a perspective view showing an embodiment of the apparatus shown in FIG. 14 with a solid pickup element array as a photoelectric conversion element and with an illumination of type (II)
Figure 19:
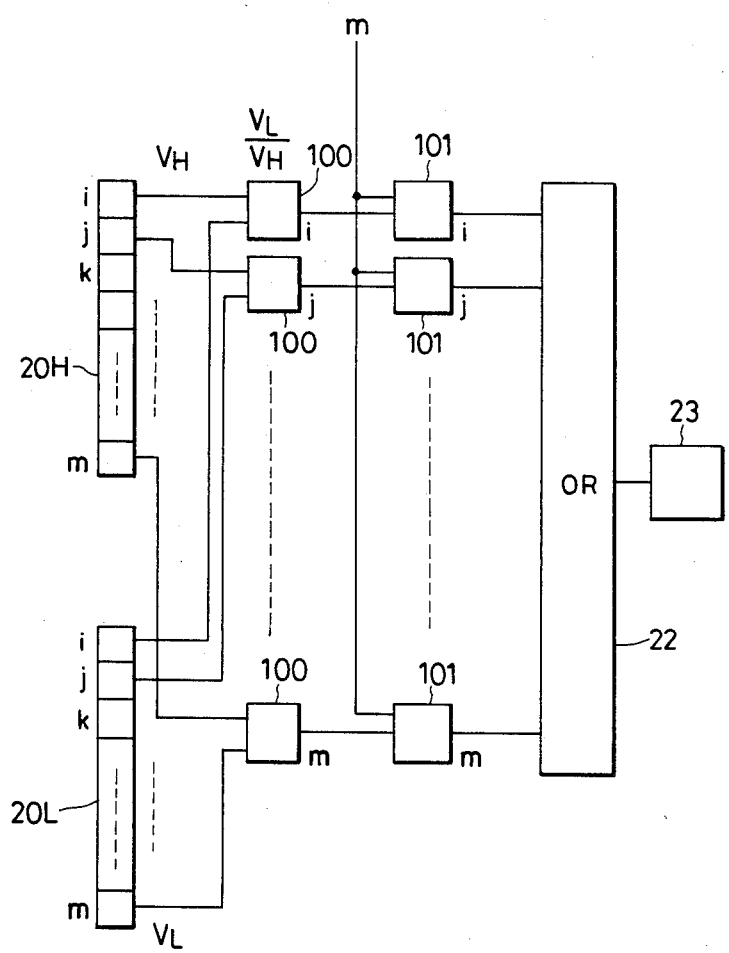
FIG. 19 shows details of an analog comparing circuit.

FIG. 19 shows the details of a signal processing circuit shown in FIG. 16. This method is the same as shown in FIG. 4.

Figure 20:
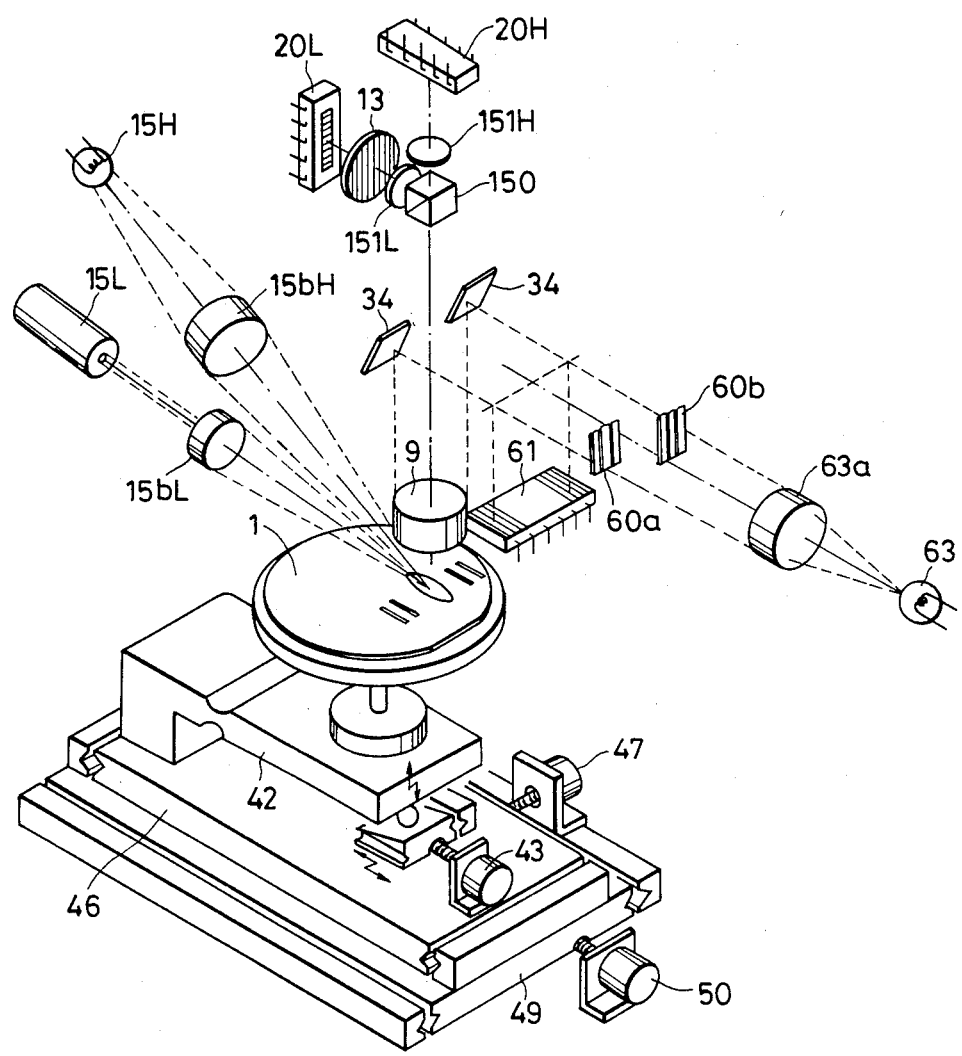
FIG. 20 is a perspective view showing a more definite constitution of an embodiment shown in FIG. 17.
Figure 21:
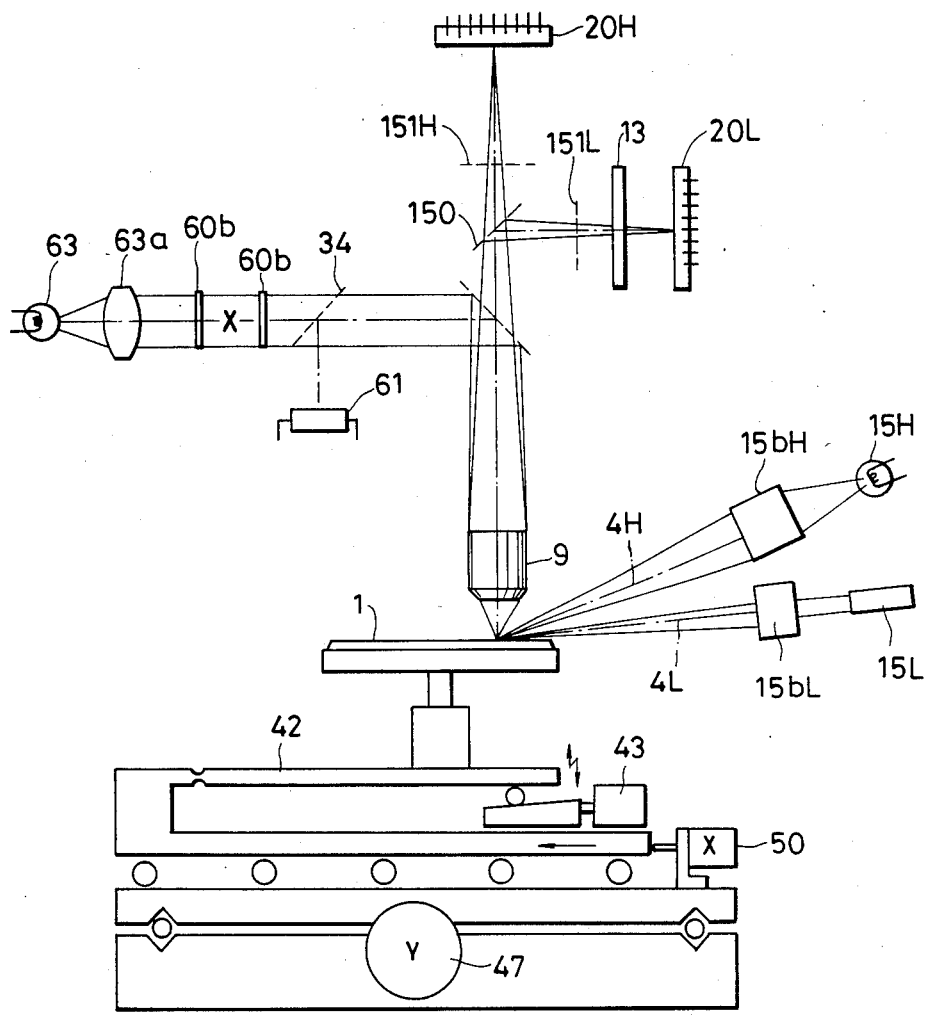
FIG. 21 is a front view of FIG. 20.
Figure 22:
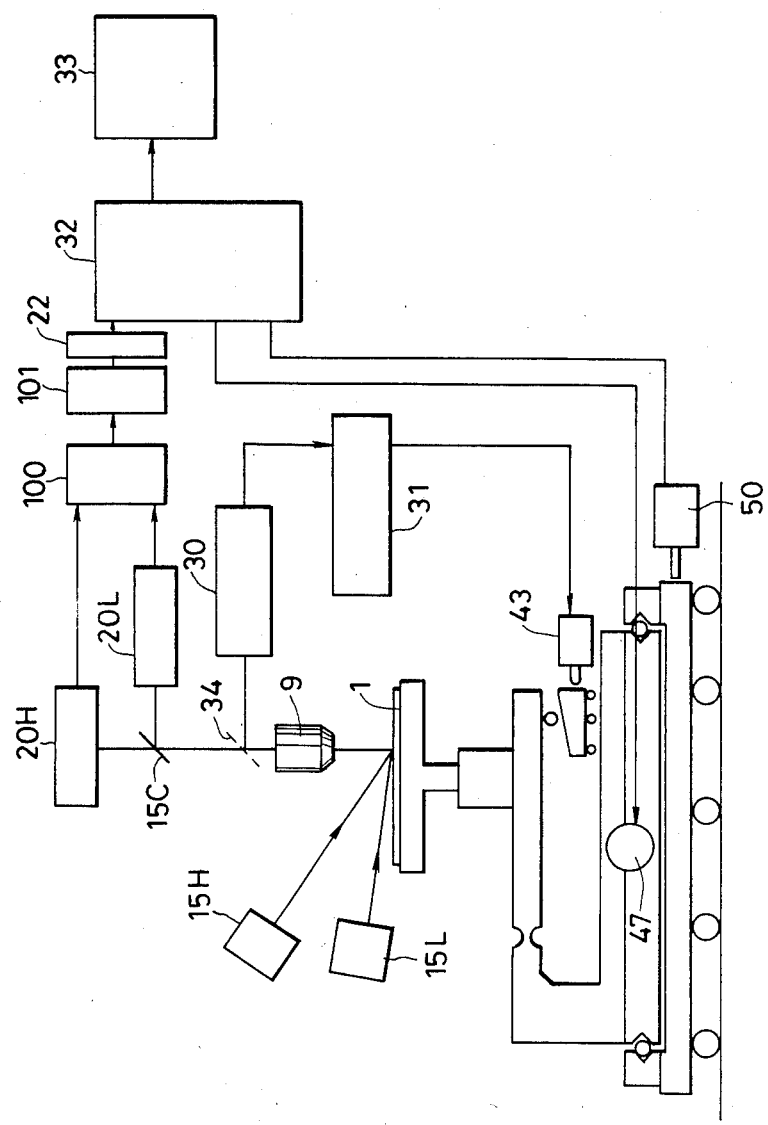
FIG. 22 shows the constitution shown in FIG. 21 and a block diagram of a signal processing circuit not shown in FIG. 21.

FIG. 20 ~ FIG. 22 are the same as FIG. 10 and FIG. 11 except that illuminating light 15H, a lens system 15 Hb, a light diverging prism 150, color filters 151H and 151L, an array 20H and an analog comparing circuit 100 are added.

An analog comparing method is hereinunder described with reference to FIG. 23 through FIG. 28.

Figure 23:
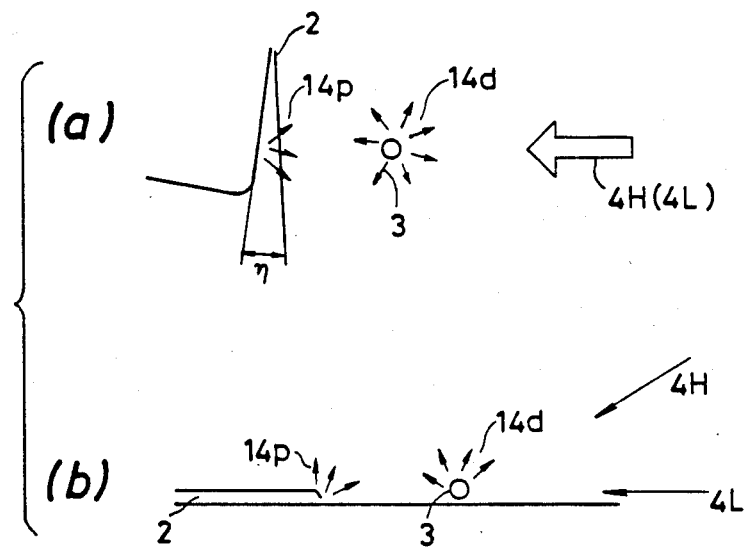
FIGS. 23(a–b) show situation of reflected light from a circuit pattern and a foreign substance.
Figure 24:
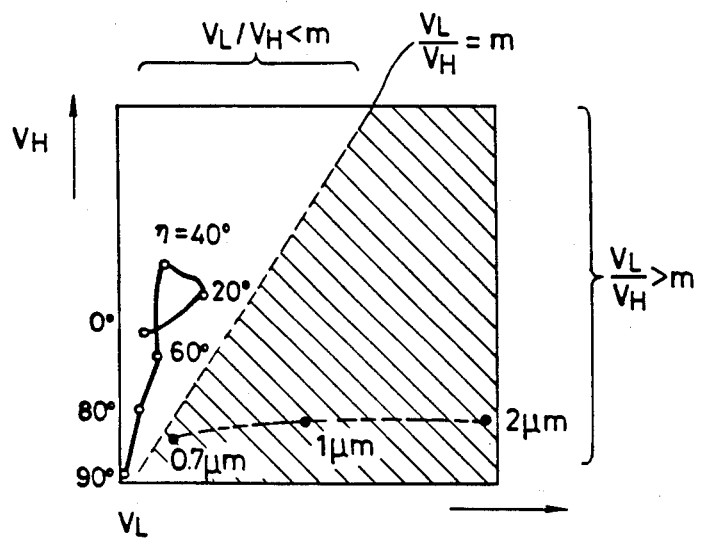
FIG. 24 shows experimental data of outputs $V_H$ and $V_L$ obtained by the reflected lights shown in FIG. 23.

FIG. 23 and FIG. 24 show the results of an experiment using the conditions given in FIG. 17. In the experiment, for an output 14p of the pattern 2, pattern outputs $V_L$ and $V_H$ were measured with the pattern 2 rotated by an angle $\eta$ from the right angle against the direction of the projection of the illuminating light 4H (4L) onto the wafer surface. Standard particles of $\phi$ 0.7, 1 and 2 $\mu$m were used as foreign substances (for foreign substances, rotation is not necessary) to measure $V_L$ and $V_H$. The measured values are shown in FIG. 24. It is understood from these results that ratio $V_L/V_H$ (white dots) of the outputs from the pattern is smaller than (m) (a reciprocal of a gradient of a broken line in the diagram). Conversely, the ratio $V_L/V_H$ (black dots) of the outputs from the foreign substance is larger than (m).

A method with which the foreign substance and the pattern are discriminated by an electrical circuit taking the output characteristics of the foreign substance and the pattern into account is described hereinunder with reference to FIG. 25 through FIG. 28.

Figure 25:
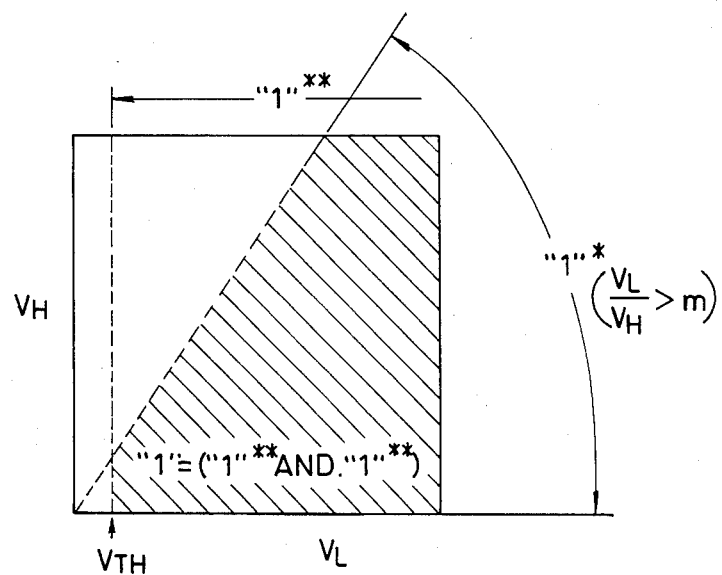
FIG. 25 shows a result of $V_H/V_L$.
Figure 26:
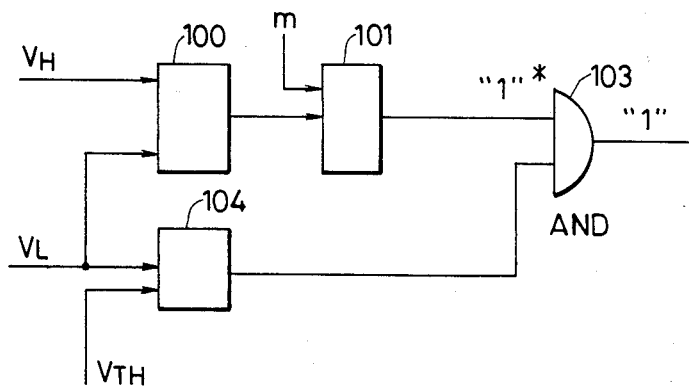
FIG. 26 shows an analog division circuit to realize $V_H/V_L$ shown in FIG. 25.

FIG. 25 and FIG. 26 show examples employing analog division circuits. The output ratio $V_L/V_H$ is processed by the analog division circuit 100 and if $V_L/V_H > m$, signal "1*" is output by a binarizing circuit 101. It must be borne in mind that, in the processing of the output ratio, when $V_H$ is small, processing error is large and the processed result becomes unstable, for instance, when $V_H$ becomes zero, $V_L/V_H = \infty$. To avoid this fact, when $V_L > V_{TH}$ ($V_{TH}$ means the value of $V_L$ corresponding to a foreign substance of about $\phi$ 0.5 $\mu$m), only "1**" is treated as effective "1" of the processed result of $V_L/V_H$. This treatment is realized by a binarizing circuit 104 and an AND circuit 103.

Figure 27:
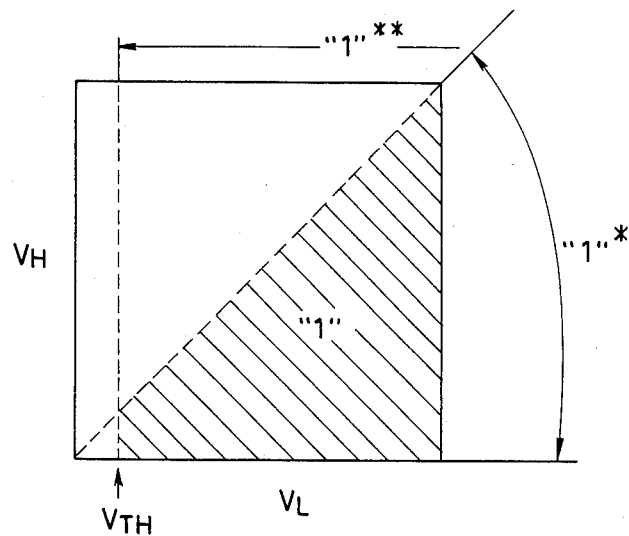
FIG. 27 shows a result of $V_L - V_H$.
Figure 28:
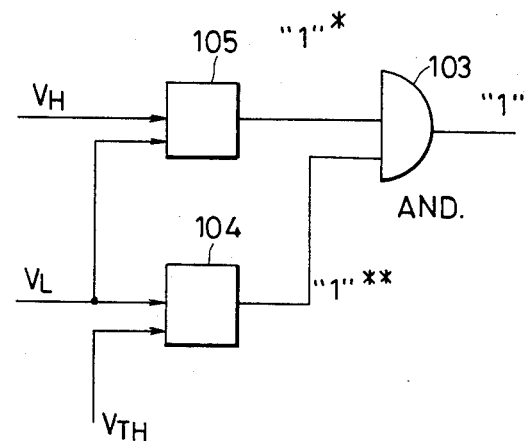
FIG. 28 shows an analog reduction circuit to realize $V_L - V_H$ shown in FIG. 27.

FIG. 27 and FIG. 28 show examples employing analog deduction circuits 105. In this case, it is important to keep m=1 (inclination of 45°) by regulating the gain of an output amplifier, not shown, of arrays 20H or 20L and regulating illumination intensity of H or L. The result $V_L - V_H$ of the analog deduction circuit is treated as effective only when the output of the binarizing circuit 104 is "1**" ($V_L > V_{TH}$) as in the previous case.

Instead of analog division and deduction mentioned above, digital value processing may be employed by A/D conversion of the output.

Figure 29:
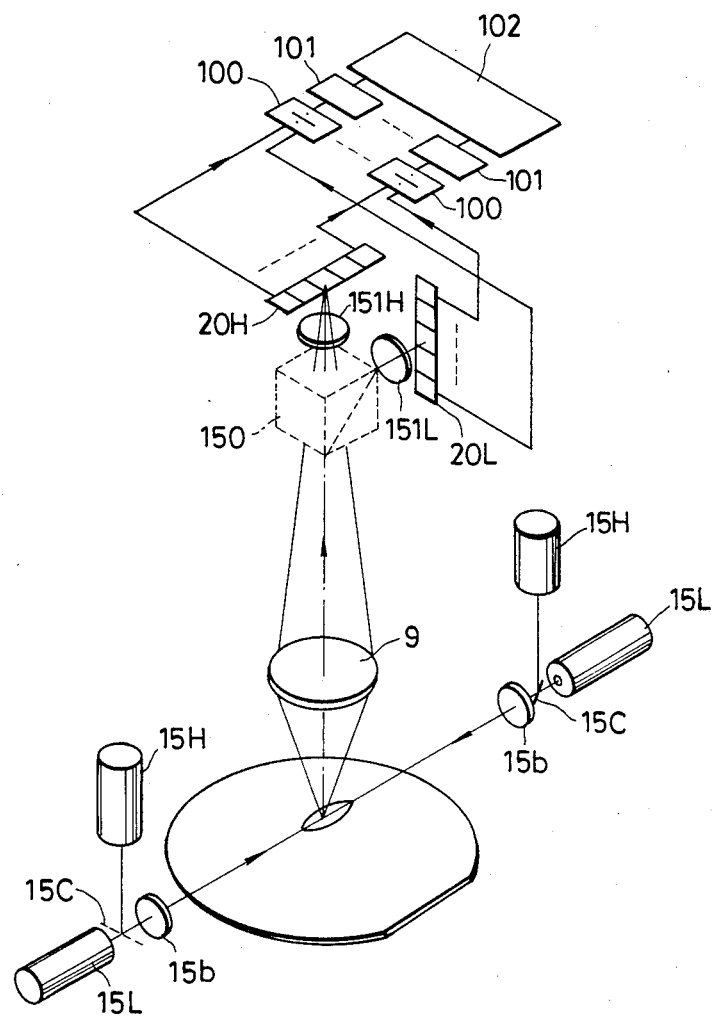
FIG. 29 is a perspective view showing illumination of type (III)

FIG. 29 shows type (III) illumination. In this case, the illuminating lights 15H and 15L have wavelengths $\lambda_1$ and $\lambda_2$ respectively and, for instance, a light diverging prism 150 and color filters 151H and 151L are employed as a spectrum decomposing optical system. A half mirror 15C of the illumination system synthesizes the illuminating lights 15H and 15L.

In the illumination and analyzed detection of types (I), (II) and (III), the conditions (A) and (B) mentioned before are indispensable as the condition (L) for emphasizing the foreign substance. On the other hand, various conditions (H) for emphasizing the pattern can be considered as shown FIG. 30(a)~(h) and FIG. 31(a)~(d). The following Table 1 shows applicability of the conditions of FIG. 30(a)~(h) and FIG. 31(a)~(d) under the conditions of types (I), (II) and (III).

TABLE 1

Figure 31:
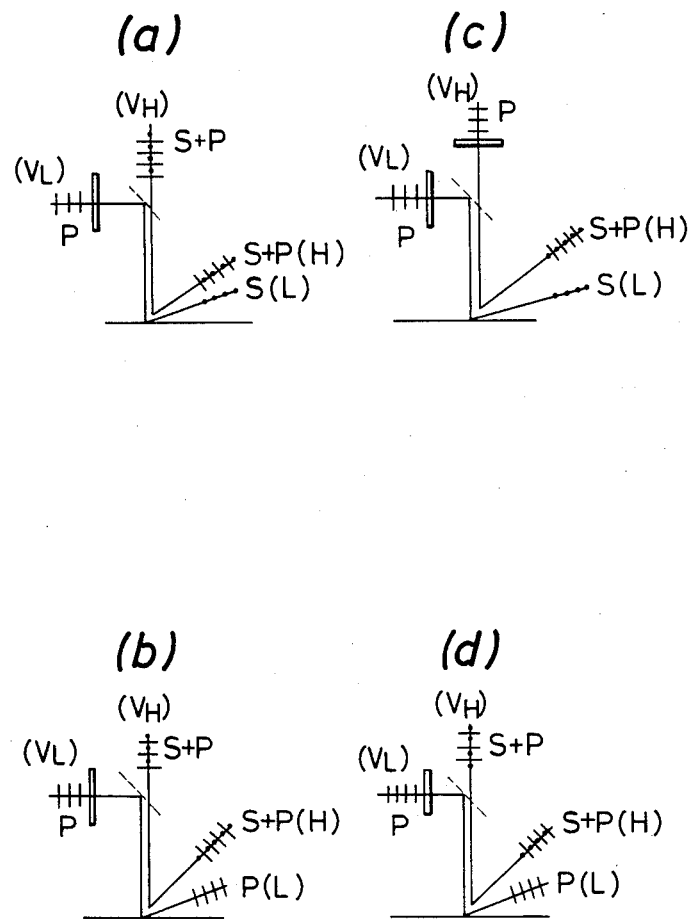

| Conditions | Types | | |
|---|---|---|---|
| | (I) | (II) | (III) |
| FIG. 30 | | | |
| (a) | o | | |
| (b) | o | o | o |
| (c) | o | o | o |
| (d) | o | | |
| (e) | o | o | o |
| (f) | o | o | |
| (g) | o | | o |
| (h) | o | | o |
| FIG. 31 | | | |
| (a) | o | | o |
| (b) | o | | o |
| (c) | o | | o |
| (d) | o | | o | o applicable

Then the conditions (L) for emphasizing the foreign substance are hereinunder discussed.

1. Analysis of Reflected Light of the Pattern

Polarized light characteristics of the reflected light of the pattern is analyzed in this chapter. At first, symbols necessary for analysis are summarized. Vector components are XYZ coordinate components. A normal vector, an incident light 4 vector and a reflected light 5 vector, a transmitted light vector of the object lens 9 and a polarized light 10 vector of the incident light are normalized.

A normal vector of the pattern 2:

$$N = [\alpha, \beta, \gamma] \quad (1)$$

$$(|N| = 1)$$

An incident light 4 vector of the pattern 2:

$$A = [\lambda, \mu, \nu] \quad (2)$$

$$(|A| = 1)$$

A reflected light 5 vector of the pattern 2:

$$B = [\rho, \delta, \tau] \ (|B| = 1) \quad (3)$$

A transmitted light vector of the object lens 9:

$$B' = [0, 0, 1] \quad (4)$$

$$(|B'| = 1)$$

A polarized light component of the incident light A:

$$E = [Ex, Ey, Ez] \quad (5)$$

$$(|E| = 1)$$

A polarized light component of the reflected light B:

$$R = [Rx, Ry, Rz] \quad (6)$$

A polarized light component 14 of the transmitted light of the object lens:

$$R' = [R'x, R'y, R'z] \quad (7)$$

An angle between the incident light and the normal N:

$$\phi \quad (8)$$

An angle between the normal N and the XY plane:

$$\epsilon \quad (9)$$

An angle between the longitudinal direction of the pattern and the X axis:

$$\eta \quad (10)$$

An angle between the reflected light B and the Z axis:

$$\psi \quad (11)$$

An angle between the X axis and a component of the reflected light projected on the XY plane:

$$\theta \quad (12)$$

An angle between the transmission axis of the analyzer and the X axis:

$$\zeta \quad (13)$$

(1) Basic Formulae of the Reflected Light of the Pattern:

Basic formulae of the reflected light of the pattern are developed with physical optics theory in this section.

FIG. 32 shows a relation between the incident light A and the reflected light B against the normal vector N on the pattern edge. Using the scalar product of the vectors, following formulae are introduced:

$$OB = -OC \quad (14)$$

$$= -(OA + AC) \quad (15)$$

$$= -\{-A + 2(A \cdot N)N\} \quad (16)$$

$$= A - 2(A \cdot N)N \quad (17)$$

Wherein the angle $\phi$ between the incident angle and the normal N is obtained from the following formulae:

$$A \cdot N = |A| \cdot |N| \cos(\pi - \phi) \quad (18)$$

$$= -\cos\phi \quad (19)$$

Substituting formulae (1) and (2) for A and N in the formula (17), following formulae are obtained as components of the vector B:

$$\begin{cases} \rho = \lambda + 2\cos\phi \times \alpha & (20) \\ \delta = \mu + 2\cos\phi \times \beta & (21) \\ \tau = \nu + 2\cos\phi \times \gamma & (22) \end{cases}$$

Change of polarized light components produced at the time of reflection is hereinunder described. According to Fresnel's reflection law, a polarized light component (electric field vector) $\mathbb{E}_s$ perpendicular to the incident plane, a plane by the incident light $\mathbb{A}$ and the normal $\mathbb{N}$, and a polarized light component $\mathbb{E}_p$ parallel to the incident plane are converted into $\mathbb{R}_s$ and $\mathbb{R}_p$ after reflection with the incident angle $\phi$ as shown in FIG. 33:

$$\begin{cases} |\mathbb{R}_s| = s(\phi)|\mathbb{E}_s| & (23) \\ |\mathbb{R}_p| = p(\phi)|\mathbb{E}_p| & (24) \end{cases}$$

Wherein coefficients $s(\phi)$ and $p(\phi)$ are given by the following formulae with a refractive index (n) of the pattern:

$$\begin{cases} s(\phi) = -\sin(\phi - \phi')/\sin(\phi + \phi') & (25) \\ p(\phi) = \tan(\phi - \phi')/\tan(\phi + \phi') & (26) \\ n\sin\phi' = \sin\phi & (27) \end{cases}$$

FIG. 34 shows calculated examples of $s(\phi)$ and $p(\phi)$ with $n = 1.5$. FIG. 34(a) shows a relation between the incident angle $\phi$ and intensity and FIG. 34(b) shows a relation between the incident angle $\phi$ and amplitude. As shown in FIG. 34(b), $s(\phi)$ is negative when $\phi = 0° \sim 90°$ but $p(\phi)$ changes from positive to negative at $\phi = \overline{\phi}$. The incident angle $\overline{\phi}$ at which $\mathbb{R}_p = 0$ is called the polarization angle. FIG. 33(a) and (b) show the comparison between the cases in which $\phi < \overline{\phi}$ and $\phi > \overline{\phi}$. Taking into consideration the fact that the relation between $\mathbb{E}_p$ and $\mathbb{R}_p$ is the same as the process with which the formula (17) was introduced, it is understood that the polarized light component $\mathbb{E}$ of the incident light and the polarized light component $\mathbb{R}$ of the reflected light conform to the following formulae To begin with, the polarized light component $\mathbb{E}$ is decomposed into component (s) and component (p):

$$\mathbb{E} = \mathbb{E}_s + \mathbb{E}_p \quad (28)$$
$$= [E_{sx}, E_{sy}, E_{sz}] + [E_{px}, E_{py}, E_{pz}] \quad (29)$$

$$\begin{cases} \mathbb{E}_s \cdot \mathbb{N} = E_{sx}\alpha + E_{sy}\beta + E_{sz}\gamma \equiv 0 & (30) \\ \mathbb{E}_s \cdot \mathbb{A} = E_{sx}\lambda + E_{sy}\mu + E_{sz}\nu \equiv 0 & (31) \\ \mathbb{E}_p \cdot \mathbb{A} = E_{px}\lambda + E_{py}\mu + E_{pz}\nu \equiv 0 & (32) \\ \mathbb{E}_s \cdot \mathbb{E}_p = E_{sx}E_{px} + E_{sy}E_{py} + E_{sz}E_{pz} \equiv 0 & (33) \end{cases}$$

Then the polarized light component of the reflected light is decomposed into component (s) and component (p):

$$\mathbb{R} = \mathbb{R}_s + \mathbb{R}_p \quad (34)$$
$$= [R_{sx}, R_{sy}, R_{sz}] + [R_{px}, R_{py}, R_{pz}] \quad (35)$$

$$\begin{cases} \mathbb{R}_s = s(\phi)\mathbb{E}_s = s(\phi)[E_{sx}, E_{sy}, E_{sz}] & (36) \\ \mathbb{R}_p = p(\phi) \times (-)\{\mathbb{E}_p - 2(\mathbb{E}_p \cdot \mathbb{N})\mathbb{N}\} & (37) \end{cases}$$
$$= -p(\phi)[E_{px} - 2K\alpha, E_{py} - 2K\beta, E_{pz} - 2K\gamma] \quad (38)$$

wherein
$$K = E_{px}\alpha + E_{py}\beta + E_{pz}\gamma (= p \cdot) \quad (39)$$

The formulae (36) and (38) are substituted for $_s$ and $_p$ in the formula (35) and following formulae are obtained:

$$\begin{cases} R_x = s(\phi)E_{sx} - p(\phi)(E_{px} - 2K\alpha) & (40) \\ R_y = s(\phi)E_{sy} - p(\phi)(E_{py} - 2K\beta) & (41) \\ R_z = s(\phi)E_{sz} - p(\phi)(E_{pz} - 2K\gamma) & (42) \end{cases}$$

Figure 35:
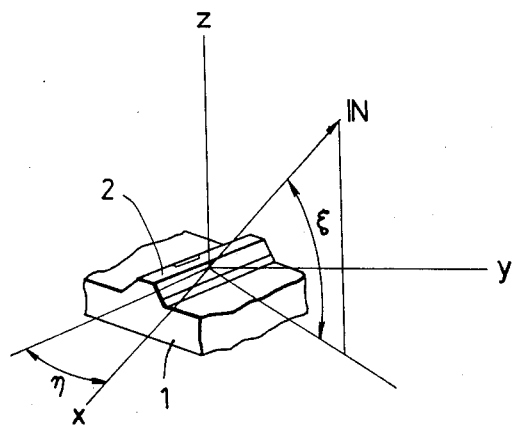
FIG. 35 is a perspective view showing a profile of the pattern.
Figure 36:
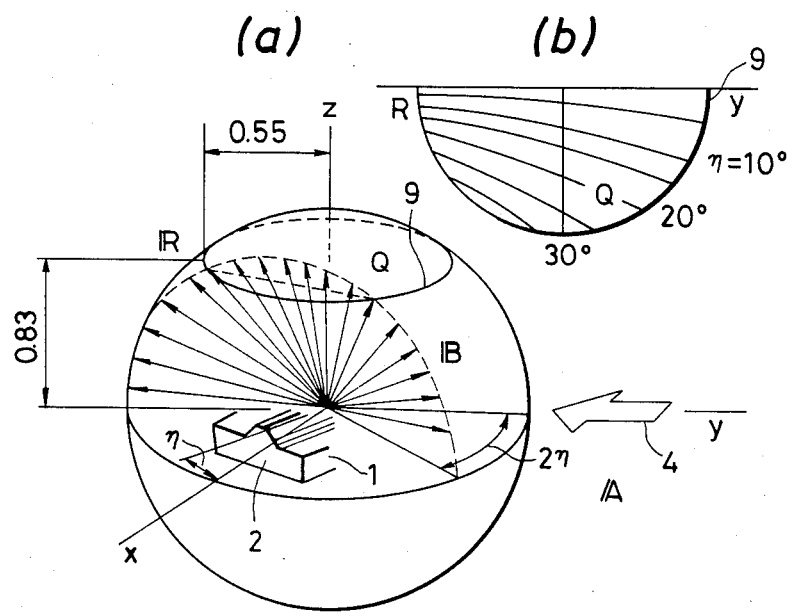
FIGS. 36(a–b) are a perspective view showing a direction of the reflected light B of the pattern and a trace of a segment RQ.

(2) Polarized Light Characteristics when the Reflected Light is Transmitted through the Object Lens:

Generally speaking, the profile of the pattern shows a smooth form as shown in FIG. 35. Therefore, the normal $\mathbb{N}$ of the pattern whose longitudinal direction and X axis defines the angle $\eta$ changes along the profile of the pattern. Diagram of FIG. 36 is obtained by changing the angle $\xi$ between the normal $\mathbb{N}$ and the XY plane continuously and by calculating the reflected light $\mathbb{B}$ corresponding to the incident light $\mathbb{A}$ along the Y axis. As shown in FIG. 36(a), if the object lens 9, for instance with N.A. = 0.55, is provided above the pattern 2, only the reflected light $\mathbb{B}$ which reaches a segment $\overline{RQ}$ in an incident pupil of the object lens enters the object lens. If a trace of the segment $\overline{RQ}$ is obtained while the angle $\eta$ is being increased, it is understood that the reflected light does not enter the object lens any more in the case of the angle $\eta > 30°$ as shown in FIG. 36(b).

The reflected light $\mathbb{B}$ which enters the object lens is refracted in the direction parallel to the Z axis as shown in FIG. 37(a) and (b). At that time, the polarized components are changed by refraction. This change is hereinunder analyzed. The refracted light is denoted by $\mathbb{B}'$ and its polarized component is denoted $R'$. The reflected polarized light component $\mathbb{R}$ is separated into a radial component $\mathbb{R}_r$ and a tangential component $R_\theta$ against the light axis Z:

$$\mathbb{R} = \mathbb{R}_r + \mathbb{R}_\theta \quad (43)$$

$$\begin{cases} \mathbb{R}_r = [\cos\theta\ R_r, \sin\theta\ R_r, R_z] & (44) \\ \mathbb{R}_\theta = [-\sin\theta\ R_\theta, \cos\theta\ R_\theta, 0] & (45) \end{cases}$$

Projected components $R_r$ and $R_\theta$ of the polarized light component $\mathbb{R}_r$ and $\mathbb{R}_\theta$ on the XY plane are obtained by the following formulae with coordinate conversion:

$$\begin{cases} R_r = \cos\theta\ R_x + \sin\theta\ R_y (= |\mathbb{R}_r|\cos\psi) & (46) \\ R_\theta = -\sin\theta\ R_x + \cos\theta\ R_y (= |\mathbb{R}_\theta|) & (47) \end{cases}$$

Wherein the polarized light component $\mathbb{R}_\theta$ is not changed by refraction but the is component $\mathbb{R}_r$ is converted into the component $\mathbb{R}_r'$ which is a vector obtained by rotating $\mathbb{R}_r$ by the angle $\psi$ with $\mathbb{R}_\theta$ as the axis of the rotation. Wherein the angle $\psi$ is the angle between the reflected light $\mathbb{B}$ and the Z-axis.

$$\mathbb{R}'_r = [\sec\psi\cos\theta R_r, \sec\psi\sin\theta R_r, 0] \quad (48)$$

From the formulae (37) and (40), the polarized light components $\mathbb{R}'$ of the refracted light $\mathbb{B}'$ are obtained by the following formulae:

$$\mathbb{R}' = \mathbb{R}'_r + \mathbb{R}_\theta = [R_x', R_y', 0] \quad (49)$$

$$= [\sec\Psi\cos\theta\, R_r - \sin\theta\, R_\theta, \sec\Psi\sin\theta\, R_r + \cos\theta\, R_\theta, 0] \quad (50)$$

$$R_x' = (\sec\Psi\,\cos^2\theta + \sin^2\theta)\, R_x + \cos\theta\sin\theta\, (\sec\Psi - 1)\, R_y \quad (51)$$

$$R_y' = \cos\theta\sin\theta\, (\sec\Psi - 1)\, R_x + (\sec\Psi\,\sin^2\theta + \cos^2\theta)\, R_y \quad (52)$$

The fact that the magnitude of the polarized light components $\mathbb{R}$ and $\mathbb{R}'$ do not change is hereinunder confirmed. Components of the reflected light $\mathbb{B}$ are expressed with the angle $\theta$ and $\psi$ as follows:

$$\mathbb{B} = [\cos\theta\times\sin\psi, \sin\theta\times\sin\psi, \cos\psi] \quad (53)$$

As the reflected light $\mathbb{B}$ and its polarized light component are perpendicular to each other, the following formula is obtained:

$$\mathbb{B}\cdot\mathbb{R} = \cos\theta\sin\psi R_x + \sin\theta\sin\psi R_y + \cos\psi R_z = 0 \quad (54)$$

From the formula (54), the magnitude of the polarized light component is obtained as follows:

$$|\mathbb{R}|^2 = R_x^2 + R_y^2 + R_z^2 \quad (55)$$

$$= R_x^2 = R_y^2 + \tan^2\Psi\, (\cos\theta\, R_x + \sin\theta\, R_y)^2 \quad (56)$$

$$= (\sin^2\theta + \sec^2\Psi\,\cos^2\theta)\, R_x^2 + (\cos^2\theta + \sec^2\Psi\,\sin^2\theta)\, R_y^2 + \sin 2\theta\tan^2\Psi\, R_x R_y \quad (57)$$

The magnitude of the polarized light component $\mathbb{R}'$ is obtained from the formulae (51) and (52) as follows:

$$|\mathbb{R}'|^2 = R'^2_x + R'^2_y \quad (58)$$

$$= \{(\sec\Psi\cos^2\theta + \sin^2\theta)\, R_x + \cos\theta\sin\theta(\sec\Psi - 1)R_y\}^2 + \{\cos\theta\sin\theta(\sec\Psi - 1)\, R_x + (\sec\Psi\sin^2\theta + \cos^2\theta)R_y\}^2 \quad (59)$$

$$= \{(\sec^2\Psi\cos^4\theta + \sin^4\theta + 2\sec\Psi\cos^2\theta\,\sin^2\theta) + \cos^2\theta\sin^2\theta\,(\sec^2\Psi - 2\sec\Psi + 1)\}\, R_x^2 + \{(\sec^2\Psi\sin^4\theta + \cos^4\theta + 2\sec\Psi\cos^2\theta\sin^2\theta) + \cos^2\theta\sin^2\theta(\sec^2\Psi - 2\sec\Psi + 1)\}\, R_y^2 + 2\,\{\cos\theta\sin\theta\,(\sec\Psi\cos^2\theta + \sin^2\theta)(\sec\Psi - 1) + \cos\theta\sin\theta(\sec\Psi - 1)\,(\sec\Psi\sin^2\theta + \cos^2\theta)\}\, R_x R_y \quad (60)$$

$$= \{\sin^2\theta(\sin^2\theta + \cos^2\theta) + \sec^2\Psi\cos^2\theta(\sin^2\theta + \cos^2\theta)\}\, R_x^2 + \{\cos^2\theta(\sin^2\theta + \cos^2\theta) + \sec^2\Psi\sin^2\theta(\sin^2\theta + \cos^2\theta)\}\, R_y^2 + 2\sin\theta\cos\theta(\sec\Psi - 1)(\sec\Psi + 1)\, R_x R_y \quad (61)$$

$$= (\sin^2\theta + \sec^2\Psi\cos^2\theta)\, R_x^2 + (\cos^2\theta + \sec^2\Psi\sin^2\theta)\, R_y^2 + \sin 2\theta\tan^2\Psi\, R_x R_y \quad (62)$$

As the formula (57) and the Formula (62) are identical, it is confirmed that the magnitude of $\mathbb{R}$ does not change even $\mathbb{R}$ is converted into $\mathbb{R}'$.

It is also confirmed that the magnitude of the polarized light component $\mathbb{R}_r$ does not change even if $\mathbb{R}_r$ is converted into $\mathbb{R}_r'$.

$$|\mathbb{R}_r|^2 = R_r^2 + R_z^2 \quad (63)$$

$$= (R_r\cos\theta)^2 + (R_r\sin\theta)^2 + R_z^2 \quad (64)$$

$$= \cos^2\theta\, (\cos\theta\, R_x + \Psi\sin\theta\, R_y)^2 + \sin^2\theta\, (\cos\theta\, R_x + \sin\theta\, R_y)^2 + \tan^2\Psi\, (\cos\theta\, R_x + \sin\theta\, R_y)^2 \quad (65)$$

$$= (1 + \tan^2\Psi)\, (\cos\theta\, R_x + \sin\theta\, R_y)^2 \quad (66)$$

$$= \sec^2\Psi\, (\cos\theta\, R_x + \sin\theta\, R_y)^2 \quad (67)$$

$$= |\mathbb{R}_r'|^2 \quad (68)$$

With the formulae described above, the magnitudes of the polarized light components produced when the reflected light $\mathbb{B}$ from the pattern with an optional angle $\theta$ transmits through the object lens are expressed by the magnitudes of the polarized light components of the incident light.

(3) Calculation when the Incident Light is Horizontal:

The polarized light components produced when the direction of the incident light $\mathbb{A}$ coincides to the Y axis are calculated in this section. In this case, the inclination angle is 0° and, as the positive reflected light from the wafer does not enter the object lens, such incident light is suitable for foreign substance detection. That is, the incident light is expressed by the following formula:

$$\mathbb{A} = [0, -1, 0] \quad (69)$$

From the formula (17), the reflected light B is expressed with the components of the normal vector N as follows:

$$\mathbb{B} = [2\alpha\beta, 2\beta^2 - 1, 2\beta\gamma] \quad (70)$$

From the formula (54), the angles $\psi$ and $\theta$ are expressed with the components of the normal vector as follows:

$$\begin{cases} \cos\psi = 2\beta\gamma \\ \cos\theta = 2\alpha\beta/\sqrt{1 - 4\beta^2\gamma^2} \end{cases} \quad (71) \\ (72)$$

The calculation is made for the cases ① $\mathbb{E}=[1, 0, 0]$ and ② $\mathbb{E}=[0, 0, 1]$. In this specification, the former is called S polarized light illumination and the latter is called P polarized light illumination.

Figure 38:
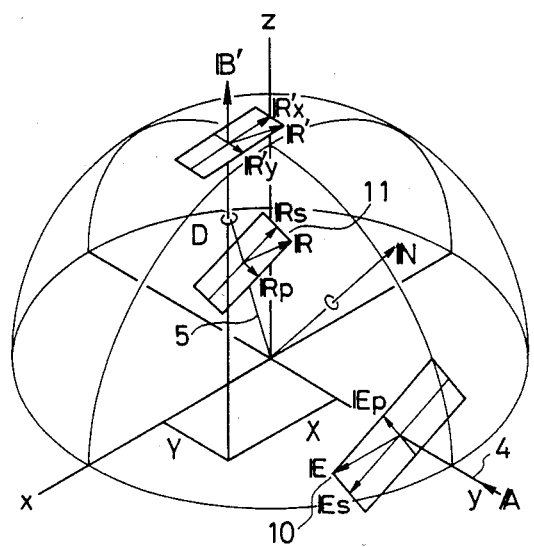
FIG. 38 is a perspective view showing polarized light of the reflected light B in the case of S polarized light illumination (wherein incident light A is A[0, −1, 0] E is E[1, 0, 0])

① S polarized light illumination ($\mathbb{E}=[1, 0, 0]$):

From the formulae (30)~(33), (s) and (p) components of the polarized light component $\mathbb{E}$ to the pattern are calculated as follows (FIG. 38):

$$\begin{cases} \mathbb{E}_p = [\alpha^2/(\alpha^2+\gamma^2), 0, \alpha\gamma/(\alpha^2+\gamma^2)] & (73) \\ \mathbb{E}_s = [\gamma^2/(\alpha^2+\gamma^2), 0, -\alpha\gamma/(\alpha^2+\gamma^2)] & (74) \end{cases}$$

From the formulae (40)~(42), the polarized light component of the reflected light is expressed by the formulae as follows:

$$\begin{cases} R_x = s(\phi)\gamma^2/(\alpha^2+\gamma^2) - p(\phi)\alpha^2(2\beta^2 - 1)/(\alpha^2+\gamma^2) & (75) \\ R_y = 2p(\phi)\alpha\beta & (76) \\ R_z = -s(\phi)\alpha\gamma/(\alpha^2+\gamma^2) - p(\phi)\alpha\gamma(2\beta^2 - 1)/(\alpha^2+\gamma^2) & (77) \end{cases}$$

The magnitude of the polarized light component is obtained from the formula (58) as follows:

$$|\mathbb{R}|^2 = \{s(\phi)\}^2\gamma^2/(\alpha^2+\gamma^2) + \{p(\phi)\}^2\alpha^2/(\alpha^2+\gamma^2) \quad (78)$$

② P polarized light illumination $\mathbb{E}=[0, 0, 1]$:

In the same process, following formulae are obtained:

$$\begin{cases} \mathbb{E}_p = [\alpha\gamma/(\alpha^2+\gamma^2), 0, \gamma^2/(\alpha^2+\gamma^2)] & (79) \\ \mathbb{E}_s = [-\alpha\gamma/(\alpha^2+\gamma^2), 0, \alpha^2/(\alpha^2+\gamma^2)] & (80) \end{cases}$$

$$\begin{cases} R_x = -s(\phi)\alpha\gamma/(\alpha^2+\gamma^2) - p(\phi)\alpha\gamma(2\beta^2 - 1)/(\alpha^2+\gamma^2) & (81) \\ R_y = 2p(\phi)\beta\gamma & (82) \\ R_z = s(\phi)\alpha^2/(\alpha^2+\gamma^2) - p(\phi)\gamma^2(2\beta^2 - 1)/(\alpha^2+\gamma^2) & (83) \end{cases}$$

$$|\mathbb{R}| = \{s(\phi)\}^2\alpha^2/(\alpha^2+\gamma^2) + \{p(\phi)\}^2\gamma^2/(\alpha^2+\gamma^2) \quad (84)$$

③ comparison between light and P polarized light illumination:

In the cases of above describe ① and ②, comparison of the polarized light components $R_x'$ and $R_y'$ at the point D on a spherical surface is hereinunder described.

If the case when the transmission axis of the analyzer element provided on the object lens is parallel to the X axis and the case when it is perpendicular to the X axis are considered, in the above mentioned case, the polarized light components which are transmitted through the analyzer are $R_x'$ and $R_y'$ in respective two cases. At that time, respective intensities of the transmitted lights are $R_x'^2$ and $R_y'^2$ respectively.

Figure 39:
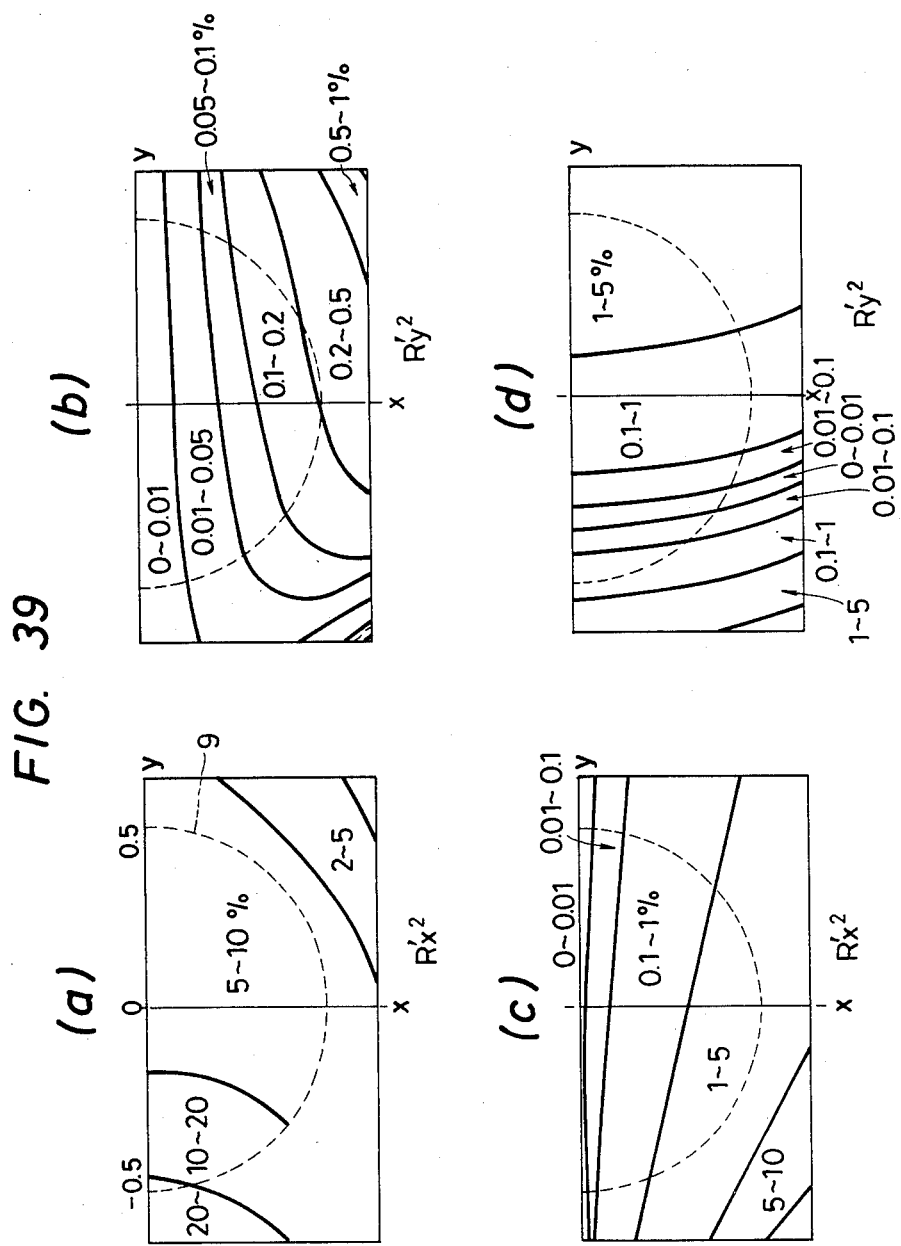
FIGS. 39(a–d) and FIGS. 40(a–d) are plan views showing distributions of polarized light components (wherein n=1.45 and n=4.2)

FIG. 39 shows intensity distribution of the transmitted light with refractive index of the pattern n=1.45 (refractive index of $SiO_2$). An incident pupil of the object lens is shown by a broken line in the drawing. As the incident light direction is identical to the Y axis in every case, the distribution is symmetrical to the Y axis. When the polarized light component (electric field vector) $\mathbb{E}$ is perpendicular to the photodetecting axis (in other words, $R_y'$ in S polarized light illumination and $R_x'$ in P polarized light illumination), the intensity is zero on the Y axis. In FIG. 39(a) and (b), transmitted light intensity distributions $R_x'^2$ and $R_y'^2$ of S polarized light illumination ($\mathbb{E}=[1, 0, ]$) are shown. FIG. 39(a) and (b) shows light intensity distributions of P polarized light illumination (E=[0, 0, 1]). Comparing $R_y^2$ of the former $R_x'^2$ of the latter, it is understood that the ratio of the maximum intensity values of the transmitted light in the incident pupil is approximately 1:10 and the reflected light intensity of the pattern is the lowest in the former case. It is interesting that, when the transmission axis is perpendicular to the X axis, the reflected light intensity $R_y'^2$ becomes zero at the semicircular part in the incident pupil.

Figure 40:
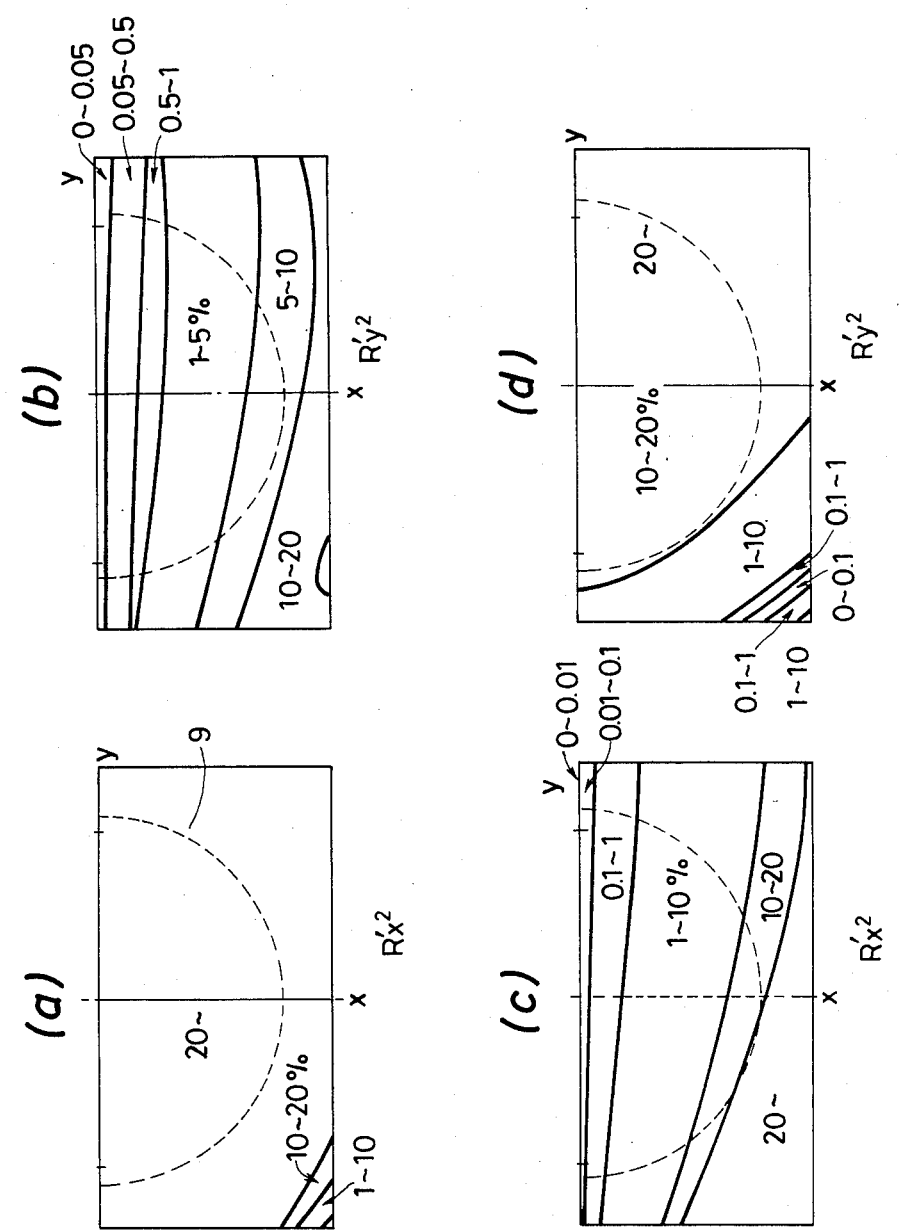

FIG. 40 shows the calculated results when the refractive index n=4.2(refractive index of polycrystalline Si). FIG. 40(a) and (b) show the results when E=[1, 0, 0] and FIG. 40(c) and (d) show the results when E=[0, 0, 1]. Compared to the results shown in FIG. 39, intensity of reflected light is higher due to the difference of refractive index but the distribution is the same.

It is understood from above discussion that the intensity of the reflected light of the pattern which transmits the object lens is the lowest when the illumination is made with S polarized light and the photodetecting axis is perpendicular to the X axis. The scattered light from the foreign substance under such conditions is not shut off by the photodetection element because the polarized light is dissolved, and as a result, the discrimination rate is expected to be the highest. This fact is hereinunder studied by experiment.

2. Study by the Experiment

Figure 41A:
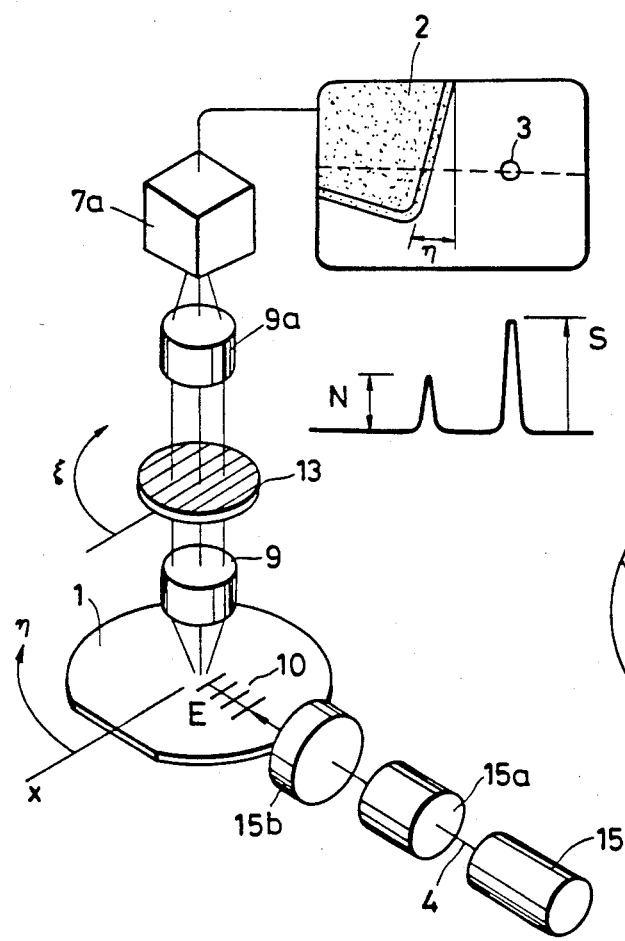
FIG. 41a and b are perspective views showing an apparatus for experiment.
Figure 41B:
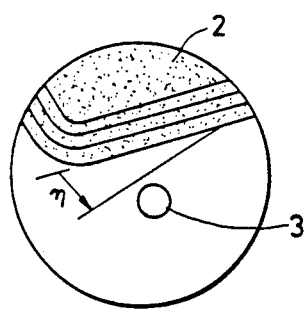

FIG. 41 shows briefly the method for the experiment. A laser spot of $\phi$ 30 $\mu$m was formed on the wafer by a He-Ne laser as illumination, a 25× beam expander and an f$\theta$ lens (f=300 mm). An angle of beam application is 2° from the horizontal plane. Magnification of the object lens was 40×(N.A.=0.55) and that of a relay lens was 2.5× and a carnicon pickup tube ($\frac{2}{3}$") was employed as a detector. The photodetection element (a polarizing plate) which could rotate freely was provided above the object lens. The wafer specimen had a polycrystalline Si pattern and an $SiO_2$ pattern and the intensity N of reflected light from edges of the patterns of polycrystalline Si and $SiO_2$ with thickness of 0.4 $\mu$m was measured. On the other hand, polystylene standard quasi particles (n=1.59) of $\phi$0.7 and 1 $\mu$m were employed as models of foreign substances and the scattered light intensity S from the models was measured. The outputs of the patterns and the foreign substances were measured in terms of N while the wafer was rotated within the rotation angle $\eta$ of 0°~180°.

Figure 42:
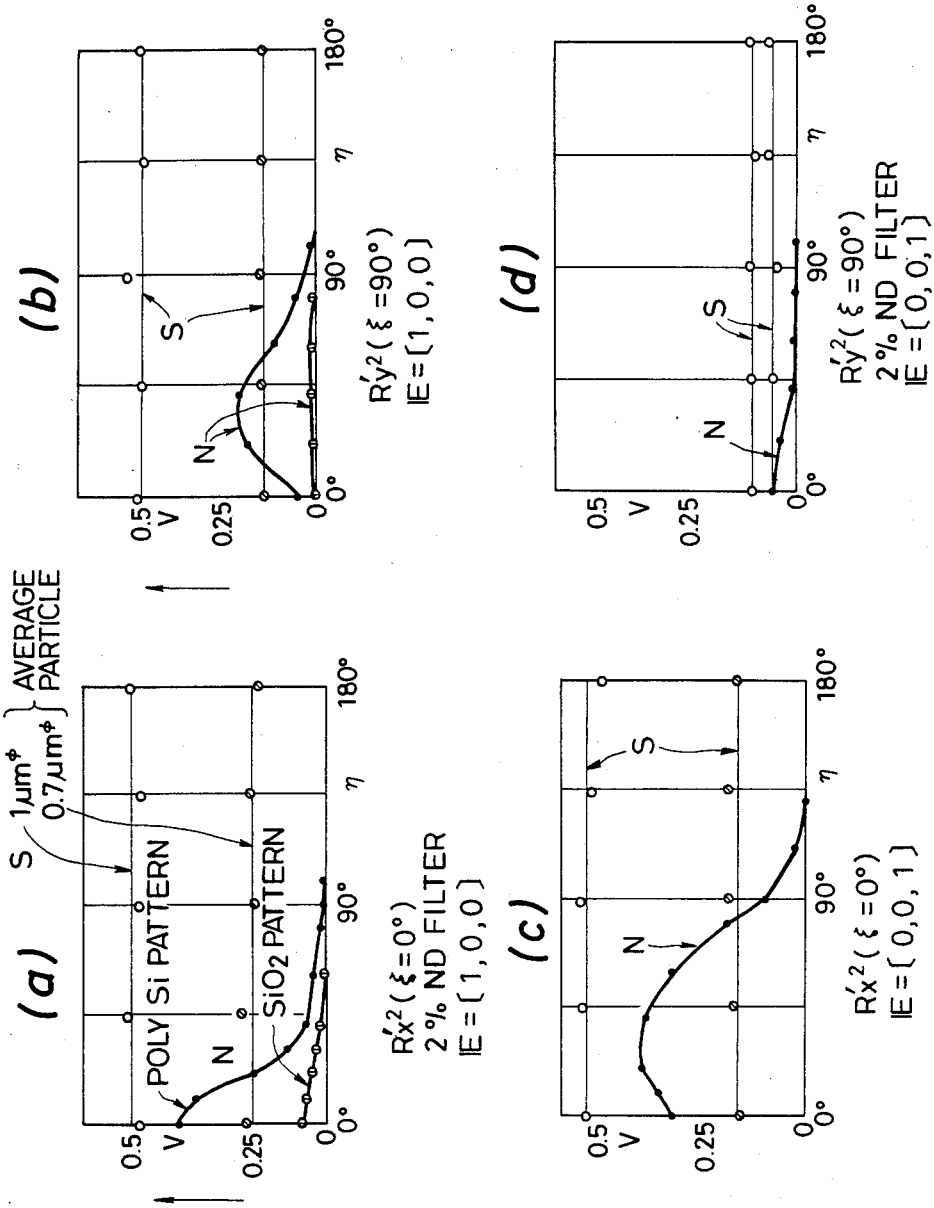
FIGS. 42(a–d) are a set of graphs showing S/N data obtained by the experiment.
Figure 43:
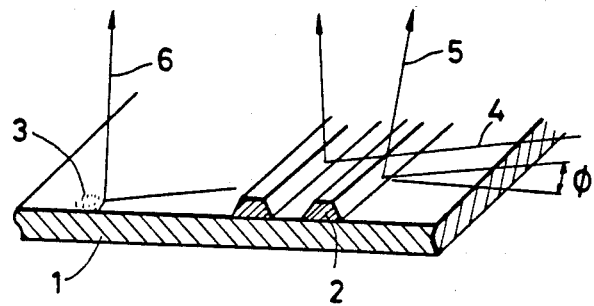
FIG. 43 is a sectional view of a wafer.
Figure 44A:
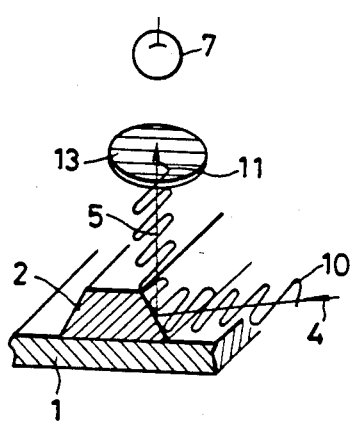
FIGS. 44(a–b) show situations of reflection of applied laser beams onto a circuit pattern and a foreign substance on the wafer.
Figure 44B:
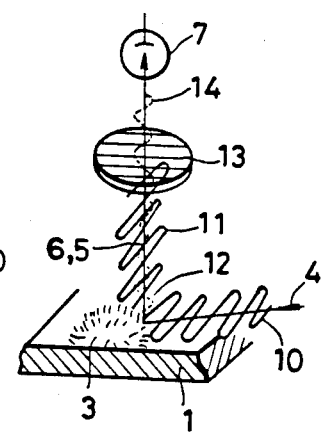
Figure 45:
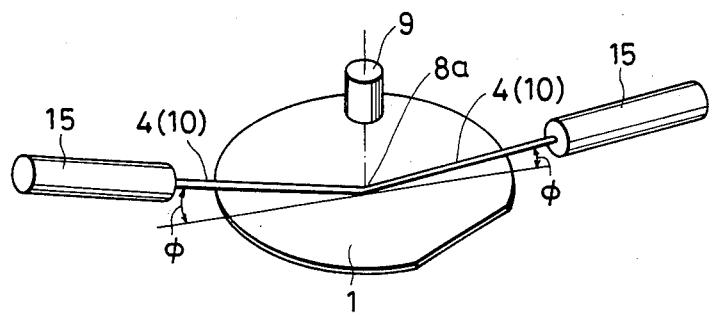
FIG. 45 is a perspective view showing briefly a first example of a method for detecting foreign substances of the prior art.

FIG. 42 shows the measured results. FIG. 42(a) and (b) show the results in the case of S polarized light illumination and FIG. 42(c) and (d) show the results in the case of P polarized light and the transmission axis is parallel or perpendicular to the X axis in each case. The ordinate of FIG. 42 represents a signal output S·N and the abscissa represents a pattern rotation angle $\eta$. An ND filter with 2% transmittance was employed in order to avoid the saturation of the pickup tube when (A) the photodetecting axis is parallel to the X axis in the case of S polarized light illumination and when (B) the photodetecting axis is perpendicular to the X axis in the case of P polarized light illumination.

It is understood from FIG. 42 that the reflected light from the pattern of $SiO_2$ becomes zero when the rotation angle $\eta$ is increased as calculated by FIG. 36 but the reflected light from the pattern of polycrystalline Si exists even when the rotation angle $\eta$ is increased nearly to 90°. This is because fine unevenness exists on the edge of the polycrystalline Si pattern as shown by an image observed by SEM in FIG. 41. In both cases, the reflected lights of the patterns show the tendency calculated by FIG. 39 (FIG. 40) but the polarized light components of the scattered lights from the foreign substances are not completely dissolved either and have the same tendency as the reflected lights from the pattern too. However, it was understood from the comparison between the scattered light output from the foreign substance of $\phi$ 1 $\mu$m and the maximum output N of the reflected light from the polycrystalline Si pattern that, in the cases shown by FIG. 39 (FIG. 40) (b) and (d), high S/N could be obtained. Considering the practical foreign substance inspection, photoelectric devices with fast detection characteristics such as a photomultiplexer and a P-I-N photodiode array are preferred to a TV camera as a detector. When the case shown by FIG. 39 (FIG. 40) (b) and the case shown by FIG. 39 (FIG. 40) (d) are compared taking above fact into account, it is understood that the output in the case (d) is about 10 times of the output in the case (b) and facilitates inspection which is not influenced by electrical noise or external disturbance light.

From above results, the most stable and sensitive inspection is facilitated when the illumination is performed by P polarized light and the photodetecting axis is perpendicular to the X axis (P polarized light component detection) and a foreign substance smaller than $\phi$ 1 $\mu$m can be detected. When the illumination is performed by S polarized light and the photodetecting axis is perpendicular to the X axis (P polarized light component detection), also high S/N can be obtained against the pattern if intensity of the illuminating light is high enough.

The application of the method and the apparatus for detecting foreign substances of the present invention is not limited to the inspection of a wafer only but is applicable to the inspection of other products such as a photomask and a reticle.

It is confirmed from the experiment that even if the size of a picture element is limited to about $10 \times 10$ $\mu m^2$, there is practically no problem when the size of a foreign substance is 1.5~2 $\mu$m.

As described above, the present invention effects the highly sensitive and stable detection of fine foreign substances on an object while maintaining the characteristic of fast foreign substance detection.

What we claim is:

1. A method for detecting foreign substances on a patterned-background on an object, comprising the steps of:

illuminating a surface of the object with at least a linear polarized laser beam at an angle inclined with respect to the surface of the object;

detecting the foreign substance with a first photoelectric conversion element providing an output indicative of scattered light from the foreign substance;

detecting the patterned-background on the object with a second photoelectric conversion element providing an output indicative of light reflected from an edge of the patterned-background;

forming a foreign substance indicating signal by non-additively processing the output of the first and second photoelectric conversion elements; and detecting the foreign substance in accordance with the foreign substance indicating signal.

2. A method for detecting foreign substances on a patterned-background on an object, comprising the steps of:

illuminating at least a surface of the object with a linear polarized laser beam at an angle inclined with respect to the surface of the object;

optically converging a scattered light from the surface of the object with an object lens;

scanning by effecting relative movement between the object and the object lens;

transmitting a scattered light of the foreign substance from the scattered light without transmitting reflected light from an edge of the patterned-background utilizing an analyzer having a transmission axis parallel to a direction of the laser beam illumination;

detecting the foreign substance on the object utilizing a semiconductor solid pickup element array arranged in a line transverse to a movement direction of the scanning; and detecting the foreign substance in accordance with a foreign substance detection signal obtained from the semiconductor solid pickup element array.

3. An apparatus for detecting foreign substances on a patterned-background on an object, comprising:

means for illuminating a surface of the object with at least a linear polarized laser beam at an angle inclined with respect to the surface of the object;

first detecting means for detecting the foreign substance on the ojbect with a first photoelectric conversion element for providing an output indicative of scattered light from the foreign substance, the first detecting means detecting the patterned-background on the object with a second photoelectric conversion element for providing an output indicative of light reflected from an edge of the patterned-background;

means for forming a foreign substance indicating signal by non-additively processing the outputs of the first and second photoelectric conversion elements; and means for detecting the foreign substance in accordance with the foreign substance indicating signal.

4. An apparatus according to claim 3, wherein said first detecting means includes an object lens for converging scattered light from the surface of the object and a diverging optical element for diverging the scattered light for the first and second photoelectric conversion elements.

5. An apparatus according to claim 4, wherein the iluminating means includes a plurality of illuminating optical systems for illuminating the object with a plurality of linear polarized laser beams at different inclination angles and at different wavelengths, the first detecting means including a spectrum-decomposing element for decomposing a spectrum of the scattered light from the surface of the object.

6. An apparatus according to claim 5, wherein the spectrum-decomposing element includes a dichroic mirror.

7. An apparatus according to claim 3, wherein the foreign substance indicating signal forming means includes means for dividing the outputs of the first and second photoelectric conversion elements.

8. An apparatus according to claim 3, wherein the foreign substance indicating signal forming means includes means for subtracting the outputs of the first and second photoelectric conversion elements.

9. An apparatus for detecting foreign substances on a patterned-background on an object, comprising:

means for illuminating a surface of the object with at least a linear polarized laser beam at an angle inclined with respect to the surface of the object;

converging means including an object lens for optically converging a scattered light from the surface of the object;

scanning means for effecting relative movement between the object and the object lens;

analyzing means for transmitting a scattered light of the foreign substance from the scattered light from the object without transmitting reflected light from an edge of the patterned-background, the analyzer means having a transmission axis parallel to a direction of the laser illumination;

a semiconductor solid pickup element array responsive to the analyzer means for detecting the scattered light of the foreign substance, the semiconductor solid pickup element array being aranged in a line transverse to a moving direction of the scanning means; and means for detecting the foreign substance by a foreign substance signal obtained from the semiconductor solid pickup element array.

* * * * *